United States Patent
Diniz De Carvalho et al.

(10) Patent No.: US 12,031,184 B2
(45) Date of Patent: *Jul. 9, 2024

(54) CANCER DETECTION AND CLASSIFICATION USING METHYLOME ANALYSIS

(71) Applicants: UNIVERSITY HEALTH NETWORK, Toronto (CA); SINAI HEALTH SYSTEM, Toronto (CA)

(72) Inventors: Daniel Diniz De Carvalho, Toronto (CA); Scott Victor Bratman, Toronto (CA); Rajat Singhania, Toronto (CA); Ankur Ravinarayana Chakravarthy, Toronto (CA); Shu Yi Shen, Markham (CA)

(73) Assignees: University Health Network, Toronto (CA); Sinai Health System, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/630,299

(22) PCT Filed: Jul. 11, 2018

(86) PCT No.: PCT/CA2018/000141
§ 371 (c)(1),
(2) Date: Jan. 10, 2020

(87) PCT Pub. No.: WO2019/010564
PCT Pub. Date: Jan. 17, 2019

(65) Prior Publication Data
US 2020/0308651 A1  Oct. 1, 2020

Related U.S. Application Data

(60) Provisional application No. 62/531,527, filed on Jul. 12, 2017.

(51) Int. Cl.
*C12Q 1/6886* (2018.01)
*C12Q 1/6827* (2018.01)
*G16B 5/20* (2019.01)
*G16B 40/00* (2019.01)
*G16B 30/20* (2019.01)

(52) U.S. Cl.
CPC ......... *C12Q 1/6886* (2013.01); *C12Q 1/6827* (2013.01); *G16B 5/20* (2019.02); *G16B 40/00* (2019.02); *C12Q 2522/10* (2013.01); *C12Q 2537/164* (2013.01); *C12Q 2600/154* (2013.01); *G16B 30/20* (2019.02)

(58) Field of Classification Search
CPC .......... C12Q 2522/10; C12Q 2537/164; C12Q 1/6886; C12Q 2600/154
See application file for complete search history.

(56) References Cited

U.S. PATENT DOCUMENTS

| | | | |
|---|---|---|---|
| 11,078,475 B2 | 8/2021 | Diniz De Carvalho et al. | |
| 11,560,558 B2 | 1/2023 | Diniz De Carvalho et al. | |
| 2003/0003455 A1 | 1/2003 | Rundell et al. | |
| 2003/0190616 A1 | 10/2003 | Goggins et al. | |
| 2011/0236903 A1* | 9/2011 | McClelland | C12Q 1/6886 435/6.14 |
| 2014/0080715 A1 | 3/2014 | Lo et al. | |
| 2016/0017419 A1* | 1/2016 | Chiu | G16B 20/20 506/2 |
| 2019/0005395 A1 | 1/2019 | Dutkowski | |
| 2020/0131582 A1 | 4/2020 | Zhou et al. | |
| 2021/0156863 A1 | 5/2021 | Dinz De Carvalho et al. | |
| 2022/0073902 A1 | 3/2022 | Diniz De Carvalho et al. | |
| 2022/0119796 A1 | 4/2022 | Diniz De Carvalho et al. | |

(Continued)

FOREIGN PATENT DOCUMENTS

| | | |
|---|---|---|
| CN | 104781422 A | 7/2015 |
| JP | 2015536639 A | 12/2015 |

(Continued)

OTHER PUBLICATIONS

Van De Voorde et al. Mutation Research. 2012. 751:304-325. (Year: 2012).*
Staunstrup et al. Clinical Epigenetics. 2016. 8:Article No. 81. (Year: 2016).*
Lisanti et al. Epigenetics. 2012. 7(6):615-625. (Year: 2012).*
Leontiou et al. PLoS ONE. 2015. 10(8):e0135058. (Year: 2015).*
OligoCalc. Retrieved from the internet: biotools.nubic.northwestern.edu/OligoCalc.html#helpMW. (Year: 2022).*
Butcher and Beck. Methods in Molecular Biology. 2017. 1589:115-138. (Year: 2017).*
Huang et al. Cancers. 2019. 11:1741, 22 pages. (Year: 2019).*
Galardi et al. Biomolecules. 2020. 10:1677. (Year: 2020).*
Diaz et al. Journal of Clinical Oncology. 2014. 32(6):579-586. (Year: 2014).*
Zhao et al. Cellular Reprogramming. 2014. 16(3):175-184. (Year: 2014).*

(Continued)

*Primary Examiner* — Joseph G. Dauner
(74) *Attorney, Agent, or Firm* — Wilson Sonsini Goodrich & Rosati

(57) ABSTRACT

There is described herein a method of detecting the presence of DNA from cancer cells in a subject comprising: providing a sample of cell-free DNA from a subject; subjecting the sample to library preparation to permit subsequent sequencing of the cell-free methylated DNA; adding a first amount of filler DNA to the sample, wherein at least a portion of the filler DNA is methylated, then optionally denaturing the sample; capturing cell-free methylated DNA using a binder selective for methylated polynucleotides; sequencing the captured cell-free methylated DNA; comparing the sequences of the captured cell-free methylated DNA to control cell-free methylated DNAs sequences from healthy and cancerous individuals and from individuals with distinct cancer types and subtypes; identifying the presence of DNA from cancer cells if there is a statistically significant similarity between one or more sequences of the captured cell-free methylated DNA and cell-free methylated DNAs sequences from cancerous individuals.

22 Claims, 23 Drawing Sheets

(56) References Cited

U.S. PATENT DOCUMENTS

| | | |
|---|---|---|
| 2022/0251665 A1 | 8/2022 | Diniz De Carvalho et al. |
| 2023/0203473 A1 | 6/2023 | Diniz De Carvalho et al. |

FOREIGN PATENT DOCUMENTS

| | | | |
|---|---|---|---|
| JP | 2017514499 A | 6/2017 | |
| WO | WO-2012143481 A2 | 10/2012 | |
| WO | WO-2014043763 A1 | 3/2014 | |
| WO | WO-2016094330 A2 | 6/2016 | |
| WO | WO-2016115530 A1 | 7/2016 | |
| WO | WO-2017008912 A1 | 1/2017 | |
| WO | WO-2017190215 A1 * | 11/2017 | ............. C12N 15/10 |
| WO | WO-2019010564 A1 | 1/2019 | |
| WO | WO-2019084659 A1 | 5/2019 | |

OTHER PUBLICATIONS

Shen et al. Nature. 2018. 563:579-583 and Methods. (Year: 2018).*
Ito et al. Nature. 2010. 466:1129-1133 and Methods. (Year: 2010).*
Wu et al. Genes & Development. 2011. 25:679-684. (Year: 2011).*
Butcher L.M. and Becks. (2015) "Nano-MeDIP-seq methylome analysis using low DNA concentrations" in: Jaggarty P., Harrison K. (eds) Population Epigenetics. Methods in Molecular Biology 1589: 115-138 Humana Press, New York, NY. ISBN: 978-1-4939-6901-2.
Burgener J. et al. (2016) "Utilization of methylated circulating tumour DNA in oral squamous cell carcinoma for risk stratification and detection of recurrence" in: TFRI-Ontario Node Research Symposium Program & Abstracts. Accessed online: < URL:htt2:// www. google.ca/url ?sa=t&rct=j&g=&esrc=s&source=web&cd=3 &cad=rja&uact=8&ved=2ahUKEwi-k5nTyrrdAhUo6IMKHVjgD9wQFjACegQICBAC&url=htt2%3A%2F%2Fwww.tfri.ca%2F docs%2F default-source%2F default-document-librarv"/o2F20 I6-sym2osiumbook. 2df%3 FsfVrsn%3D6 &usg=AOvVaw2jPwjGZr.
De Carvalho D. May 16, 2017 (May 16, 2017) "Real-time liquid biopsy cancer diagnosis and monitoring" Flintbox. accessed online: <URL:https://www.flintbox.com/public/project/31470/ >.
Diaz, L.A., Jr. and A. Bardelli, Liquid biopsies: genotyping circulating tumor DNA. Journal of Clinical Oncology, Feb. 20, 2014, vol. 32(6): pp. 579-586.
Lehmann-Werman, R., et al., Identification of tissue-specific cell death using methylation patterns of circulating DNA. Proceedings of the National Academic of Sciences of U.S.A., Published on line Mar. 14, 2016, pp. E1826-E1834.
Visvanathan, K., et al., Monitoring of Serum DNA Methylation as an Early Independent Marker of Response and Survival in Metastatic Breast Cancer: TBCRC 005 Prospective Biomarker Study. Journal of Clinical Oncology, Mar. 1, 2017, vol. 35(7): pp. 751-758.
Newman, A.M., et al., An ultrasensitive method for quantitating circulating tumor DNA with broad patient coverage. Nat Med, 2014 Ma; 20(5): pp. 548-554.
Aravanis, A.M., M. Lee, and R.D. Klausner, Next-Generation Sequencing of Circulating Tumor DNA for Early Cancer Detection. Cell, 168; Feb. 9, 2017. 168(4): pp. 571-574.
Mack, S.C., et al., Epigenomic alterations define lethal CIMP-positive ependymomas of infancy. Nature, Feb. 27, 2014; 506(7489): pp. 445-450.
Lienhard, M., et al., MEDIPS: genome-wide differential coverage analysis of sequencing data derived from DNA enrichment experiments. Bioinformatics, 2014. vol. 30(2): pp. 284-286.
Law, C.W., et al., voom: Precision weights unlock linear model analysis tools for RNA-seq read counts. Genome Biol, 2014. 15(2); R2. pp. 1-17.
Chakravarthy, A., et al., Human Papillomavirus Drives Tumor Development Throughout the Head and Neck: Improved Prognosis Is Associated With an Immune Response Largely Restricted to the Oropharynx. Journal of Clinical Oncology, Dec. 1, 2016; vol. 34(34): pp. 4132-4141.

Hoadley, K.A., et al., Multiplatform analysis of 12 cancer types reveals molecular classification within and across issues of origin. Cell, Aug. 14, 2014. 158(4): pp. 929-944.
Fleischhacker, M. and B. Schmidt, Circulating nucleic acids (CNAs) and cancer—a survey. Biochimica et Biophysica Acta, 2007. 1775(1): pp. 181-232.
Potter, N.T., et al., Validation of a real-time PCR-based qualitative assay for the detection of methylated SEPT9 DNA in human plasma. Clinical Chemistry 2014. 60(9): pp. 1183-1191.
Legendre, C., et al., Whole-genome bisulfite sequencing of cell-free DNA identifies signature associated with metastatic breast cancer. Clinical Epigenetics, 2015. 7:100; pp. 1-10.
Sun, K., et al., Plasma DNA tissue mapping by genome-wide methylation sequencing for noninvasive prenatal, cancer, and transplantation assessments. Proceedings of the National Academic of Sciences of U.S.A., Published on line Sep. 21, 2015. 112(40): pp. E5503-E5512.
Chan, K.C., et al., Noninvasive detection of cancer-associated genome-wide hypomethylation and copy number aberrations by plasma DNA bisulfite sequencing. Proceedings of the National Academic of Sciences of U.S.A., Published Nov. 19, 2013. 110(47): pp. 18761-18768.
Sharma, S., T.K. Kelly, and P.A. Jones, Epigenetics in cancer. Carcinogenesis, 2010. vol. 31(1): pp. 27-36.
Sturm, D., et al., Hotspot mutations in H3F3A and IDH1 define distinct epigenetic and biological subgroups of glioblastoma. Cancer Cell, Oct. 16, 2012. vol. 22(4): p. 425-437.
Hinoue, T., et al., Genome-scale analysis of aberrant DNA methylation in colorectal cancer. Genome Research, 2012. 22(2): pp. 271-282.
Stirzaker, C., et al., Methylome sequencing in triple-negative breast cancer reveals distinct methylation clusters with prognostic value. Nature Communications; Feb. 2, 2015. 6:5899; pp. 1-11.
Fang, F., et al., Breast cancer methylomes establish an epigenomic foundation for metastasis. Sci Transl Med, Mar. 23, 2011; vol. 3(75): p. 75ra25; pp. 1-22.
Laurens van der Maaten, G.H., Visualizing Data using t-SNE. Journal of Machine Learning Research 9. Nov. 2008: pp. 2579-2605.
Kandoth, C., et al., Mutational landscape and significance across 12 major cancer types. Nature, Oct. 17, 2013; 502 (7471): pp. 333-339.
McGranahan, N., et al., Clonal status of actionable driver events and the timing of mutational processes in cancer evolution. Sci Transl Med, Apr. 15, 2015. 7(283): p. 283ra54; pp. 1-22.
Zauber, P., S. Marotta, and M. Sabbath-Solitare, KRAS gene mutations are more common in colorectal villous adenomas and in situ carcinomas than in carcinomas. Int J Mol Epidemiol Genet, 2013. 4(1): pp. 1-10.
Martincorena, I., et al., Tumor evolution. High burden and pervasive positive selection of somatic mutations in normal human skin. Science, May 22, 2015. 348(6237): pp. 880-886.
Beltran, H., et al., Divergent clonal evolution of castration-resistant neuroendocrine prostate cancer. Mar. 2016; 22(3): pp. 298-305.
Taiwo, O., et al., Methylome analysis using MeDIP-seq with low DNA concentrations. Nature Protocols, Mar. 8, 2012. vol. 7(4): pp. 617-636.
Akalin et al. MethylKit: A Comprehensive R Package for the Analysis of Genome-Wide DNA Methylation Profiles. Genome Biology 13(10):R87 (2012).
Bailey, et al. Genomic analyses identify molecular subtypes of pancreatic cancer. Nature. Mar. 3, 2016;531(7592):47-52. doi: 10.1038/nature16965. Epub Feb. 24, 2016.
Chiu, et al. Noninvasive prenatal diagnosis of fetal chromosomal aneuploidy by massively parallel genomic sequencing of DNA in maternal plasma. Proc Natl Acad Sci USA. Dec. 23, 2008;105(51):20458-20463. doi: 10.1073/pnas.0810641105. Epub Dec. 10, 2008.
Co-pending U.S. Appl. No. 17/668,314, inventors De Carvalho; Daniel Diniz et al., filed on Feb. 9, 2022.
European search report and opinion dated Mar. 23, 2021 for EP Application No. 18832886.8.
European search report and opinion dated Oct. 31, 2019 for EP Application No. 17792306.7.

(56) References Cited

OTHER PUBLICATIONS

Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Feber, et al. Comparative methylome analysis of benign and malignant peripheral nerve sheath tumors. Genome Res. Apr. 2011; 21(4): 515-524. doi: 10.1101/gr.109678.110.
Fraga, et al. The affinity of different MBD proteins for a specific methylated locus depends on their intrinsic binding properties. Nucleic Acids Res. Mar. 15, 2003;31(6):1765-1774. doi: 10.1093/nar/gkg249.
Gao, et al. miR-615-5p is epigenetically inactivated and functions as a tumor suppressor in pancreatic ductal adenocarcinoma. Oncogene. Mar. 26, 2015;34(13):1629-1640. doi: 10.1038/onc.2014.101. Epub Apr. 28, 2014.
Gonzalgo, et al. Identification and characterization of differentially methylated regions of genomic DNA by methylation-sensitive arbitrarily primed PCR. Cancer Res. Feb. 15, 1997;57(4):594-599.
GTEx Consortium. Human genomics. The Genotype-Tissue Expression (GTEx) pilot analysis: multitissue gene regulation in humans. Science. May 8, 2015;348(6235):648-660. doi: 10.1126/science.1262110. Epub May 7, 2015.
Gu, et al. Preparation of reduced representation bisulfite sequencing libraries for genome-scale DNA methylation profiling. Nat Protoc. Apr. 2011;6(4):468-81. doi: 10.1038/nprot.2010.190. Epub Mar. 18, 2011.
Heinz, et al. Simple combinations of lineage-determining transcription factors prime cis-regulatory elements required for macrophage and B cell identities. Mol Cell. May 28, 2010;38(4):576-589. doi: 10.1016/j.molcel.2010.05.004.
Heyn, et al. DNA methylation profiling in the clinic: applications and challenges. Nature Reviews Genetics 13(10):679-692 (2012).
Hu, et al. DNA methylation presents distinct binding sites for human transcription factors. Elife. Sep. 3, 2013;2:e00726. doi: 10.7554/eLife.00726.
Hung, et al. Detection of circulating fetal nucleic acids: a review of methods and applications. J Clin Pathol. Apr. 2009;62(4):308-313. doi: 10.1136/jcp.2007.048470.
International search report with written opinion dated Jun. 28, 2017 for PCT/CA2017/000108.
International search report with written opinion dated Oct. 3, 2018 for PCT/CA2018/000141.
Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.
Lui, et al. Predominant hematopoietic origin of cell-free DNA in plasma and serum after sex-mismatched bone marrow transplantation. Clin Chem. Mar. 2002;48(3):421-427.
Mikeska, et al. DNA methylation biomarkers: cancer and beyond. Genes (Basel). Sep. 16, 2014;5(3):821-864. doi: 10.3390/genes5030821.
Neary, et al. Comparative analysis of MBD-seq and MeDIP-seq and estimation of gene expression changes in a rodent model of schizophrenia. Genomics. Jul. 2017;109(3-4):204-213. doi: 10.1016/j.ygeno.2017.03.004. Epub Mar. 29, 2017.
Notice of Allowance dated Mar. 19, 2021 for U.S. Appl. No. 16/098,620.
Office action dated Jan. 28, 2022 for U.S. Appl. No. 17/519,350.
Office action dated Jun. 25, 2020 for U.S. Appl. No. 16/098,620.
Office action dated Dec. 21, 2020 for U.S. Appl. No. 16/098,620.
Rauch, et al. MIRA-assisted microarray analysis, a new technology for the determination of DNA methylation patterns, identifies frequent methylation of homeodomain-containing genes in lung cancer cells. Cancer Res. Aug. 15, 2006;66(16):7939-7947. doi: 10.1158/0008-5472.CAN-06-1888.
Schwarzenbach, et al. Cell-free nucleic acids as biomarkers in cancer patients. Nat Rev Cancer. Jun. 2011;11(6):426-437. doi: 10.1038/nrc3066. Epub May 12, 2011.
Snyder et al. Cell-free DNA Comprises an In Vivo Nucleosome Footprint that Informs Its Tissues-Of-Origin. Cell 164:57-68 (2016).
Snyder, et al. Universal noninvasive detection of solid organ transplant rejection. Proc Natl Acad Sci U S A. Apr. 12, 2011;108(15):6229-34. doi: 10.1073/pnas.1013924108. Epub Mar. 28, 2011.
Su, et al., "A gene atlas of the mouse and human protein-encoding transcriptomes", Proc Natl Acad Sci USA, Apr. 20, 2004, pp. 6062-6067, 101 (16).
Varley, et al. Dynamic DNA methylation across diverse human cell lines and tissues. Genome Res. Mar. 2013;23(3):555-567. doi: 10.1101/gr.147942.112. Epub Jan. 16, 2013.
Wu, et al. BioGPS: building your own mash-up of gene annotations and expression profiles. Nucleic Acids Res. Jan. 4, 2016;44(D1):D313-316. doi: 10.1093/nar/gkv1104. Epub Nov. 17, 2015.
Xiang, et al. DNA methylome profiling of maternal peripheral blood and placentas reveal potential fetal DNA markers for non-invasive prenatal testing. Mol Hum Reprod. Sep. 2014;20(9):875-884. doi: 10.1093/molehr/gau048. Epub Jul. 4, 2014.
Yagi, et al. DNA methylation profile of tissue-dependent and differentially methylated regions (T-DMRs) in mouse promoter regions demonstrating tissue-specific gene expression. Genome Res. Dec. 2008;18(12):1969-1978. doi: 10.1101/gr.074070.107. Epub Oct. 29, 2008.
Zhao, et al. Methylated DNA immunoprecipitation and high-throughput sequencing (MeDIP-seq) using low amounts of genomic DNA. Cell Reprogram. Jun. 2014;16(3):175-184. doi: 10.1089/cell.2014.0002. Epub Apr. 28, 2014.
Chen, et al. A Study of Cell-free DNA Fragmentation Pattern and Its Application in DNA Sample Type Classification. IEEE/ACM Trans Comput Biol Bioinform. Jul. 4, 2017. doi: 10.1109/TCBB.2017.2723388. Online ahead of print.
Co-pending U.S. Appl. No. 18/059,370, inventors Diniz; De Carvalho Daniel et al., filed on Nov. 28, 2022.
Co-pending U.S. Appl. No. 18/061,273, inventors Diniz; De Carvalho T. Daniel et al., filed on Dec. 2, 2022.
Notice of Allowance dated Aug. 31, 2022 for U.S. Appl. No. 17/519,350.
Notice of Allowance dated Sep. 15, 2022 for U.S. Appl. No. 17/519,350.
Office action dated Jun. 1, 2022 for U.S. Appl. No. 17/519,350.
Office action dated Jun. 29, 2022 for U.S. Appl. No. 17/668,314.
Shamay, et al. CpG methylation as a tool to characterize cell-free Kaposi sarcoma herpesvirus DNA. J Infect Dis. Apr. 1, 2012;205(7):1095-1099. doi: 10.1093/infdis/jis032. Epub Feb. 22, 2012.
Warton, et al. Methylation of cell-free circulating DNA in the diagnosis of cancer. Front Mol Biosci. Apr. 22, 2015;2:13. doi: 10.3389/fmolb.2015.00013. eCollection 2015.
Weisenberger, D. Characterizing DNA methylation alterations from The Cancer Genome Atlas. J Clin Invest. Jan. 2014;124(1):17-23. doi: 10.1172/JCI69740. Epub Jan. 2, 2014.
Bewick, et al. Statistics review 13: receiver operating characteristic curves. Crit Care. Dec. 2004;8(6):508-12. Epub Nov. 4, 2004.
Borgel, et al. Targets and Dynamics of Promoter DNA Methylation During Early Mouse Development, Nature Genetics 42 (2010): 1093-1101.
Daniels, et al. New Map of Bacteriophase Lambda DNA. Journal of Virology, Jan. 1980, p. 390-400.
Kirkwood, et al. Immunotherapy of cancer in 2012. CA Cancer J Clin. Sep.-Oct. 2012;62(5):309-35. doi: 10.3322/caac.20132. Epub May 10, 2012.
Liang, et al. Non-invasive diagnosis of early-stage lung cancer using high-throughput targeted DNA methylation sequencing of circulating tumor DNA (ctDNA). Theranostics vol. 9, Issue 7, pp. 2056-2070 (Apr. 6, 2019).
Schatz, et al. Cloud computing and the DNA data race. Nature Biotechnology, vol. 28, No. 7, Jul. 2010. p. 691-693.
U.S. Appl. No. 18/061,273 Office Action dated Jul. 19, 2023.
Wu, et al. A novel cell-free DNA methylation-based model improves the early detection of colorectal cancer. Molecular Oncology 15 (2021) 2702-2714.
ZYMO Research. 5-Methylcytosine & 5-Hydroxymethylcytosine DNA Standard Set. 2010. 2 pages.
Bagley, et al. Pretreatment neutrophil-to-lymphocyte ratio as a marker of outcomes in nivolumab-treated patients with advanced

(56) References Cited

OTHER PUBLICATIONS non-small-cell lung cancer. Lung Cancer. Apr. 2017;106:1-7. doi: 10.1016/j.lungcan.2017.01.013. Epub Jan. 25, 2017.

Bettegowda et al. Detection of Circulating Tumor DNA in Early- and Late-Stage Human Malignancies. Sci. Transl. Med. 6(224):224ra24 (2014).

Brena, et al. Toward a human epigenome. Nat Genet. Dec. 2006;38(12):1359-1360. doi: 10.1038/ng1206-1359.

Bupathi et al. Biomarkers for immune therapy in colorectal cancer: mismatch-repair deficiency and others. Journal of Gastrointestinal Oncology 2016;7(5):713-720.

Cassidy, et al. Neutrophil to Lymphocyte Ratio is Associated With Outcome During Ipilimumab Treatment. EBioMedicine. Apr. 2017; 18:56-61. doi: 10.1016/j.ebiom.2017.03.029. Epub Mar. 24, 2017.

Christensen, et al. DNA methylation, isocitrate dehydrogenase mutation, and survival in glioma. J Natl Cancer Inst. Jan. 19, 2011;103(2):143-153. doi: 10.1093/jnci/djq497. Epub Dec. 16, 2010.

Di Giacomo, et al. Long-term survival and immunological parameters in metastatic melanoma patients who responded to ipilimumab 10 mg/kg within an expanded access programme. Cancer Immunol Immunother. Jun. 2013;62(6):1021-1028. doi: 10.1007/s00262-013-1418-6. Epub Apr. 17, 2013.

Eckhardt, et al. DNA methylation profiling of human chromosomes 6, 20 and 22. Nat Genet. Dec. 2006; 38(12): 1378-1385. Published online Oct. 29, 2006. doi: 10.1038/ng1909.

EP18874092.2 Extended European Search Report dated Jul. 5, 2021.

Esteller, et al. Inactivation of the DNA-repair gene MGMT and the clinical response of gliomas to alkylating agents. N Engl J Med. Nov. 9, 2000;343(19):1350-1354. doi: 10.1056/NEJM200011093431901.

Ferrucci, et al. Baseline neutrophils and derived neutrophil-to-lymphocyte ratio: prognostic relevance in metastatic melanoma patients receiving ipilimumab. Ann Oncol. Apr. 2016;27(4):732-738. doi: 10.1093/annonc/mdw016. Epub Jan. 22, 2016.

Flusberg, et al. Direct Detection of DNA Methylation During Single-molecule, Real-time Sequencing. Nature Methods 7 (2010): 461-465.

Gevaert, et al. Pancancer analysis of DNA methylation-driven genes using MethylMix. Genome Biol. Jan. 29, 2015;16(1):17. doi: 10.1186/s13059-014-0579-8.

Gosho, et al. Study Designs and Statistical Analyses for Biomarker Research. Sensors (Basel). 2012; 12(7): 8966-8986. Published online Jun. 29, 2012. doi: 10.3390/s120708966.

Graves, et al. Quantitative and qualitative analysis of [(18)F]FDG and [(18)F]FAZA positron emission tomography of head and neck cancers and associations with HPV status and treatment outcome. Eur J Nucl Med Mol Imaging. Apr. 2016;43(4):617-625. doi: 10.1007/s00259-015-3247-7. Epub Nov. 18, 2015.

Hegi et al., MGMT Gene Silencing and Benefit from Temozolomide in Glioblastoma. The New England Journal of Medicine 352(10): 997-1003 (2005).

Houseman, et al. Reference-free deconvolution of DNA methylation data and mediation by cell composition effects. BMC Bioinformatics. Jun. 29, 2016;17:259. doi: 10.1186/s12859-016-1140-4.

Hughey et al. Robust meta-analysis of gene expression using the elastic net. Nucleic Acids Research 2015, vol. 43, No. 12, e79, 11 pages.

International Search Report regarding PCT patent application No. PCT/CA2018/000141, dated Oct. 3, 2018 issued by ISA/CA (CIPO).

International Search Report regarding PCT patent application No. PCT/CA2018/000203, dated Feb. 14, 2019 issued by ISA/CA (CIPO).

Koestler, et al. DNA Methylation-Derived Neutrophil-to-Lymphocyte Ratio: An Epigenetic Tool to Explore Cancer Inflammation and Outcomes. Cancer Epidemiol Biomarkers Prev. Mar. 2017;26(3):328-338. doi: 10.1158/1055-9965.EPI-16-0461. Epub Dec. 13, 2016.

Kuzman, et al. Neutrophil-lymphocyte ratio as a predictive biomarker for response to high dose interleukin-2 in patients with renal cell carcinoma. BMC Urol. Jan. 5, 2017;17(1):1. doi: 10.1186/s12894-016-0192-0.

Lee, et al. Strategy of Using Intratreatment Hypoxia Imaging to Selectively and Safely Guide Radiation Dose De-escalation Concurrent With Chemotherapy for Locoregionally Advanced Human Papillomavirus-Related Oropharyngeal Carcinoma. Int J Radiat Oncol Biol Phys. Sep. 1, 2016;96(1):9-17. doi: 10.1016/j.ijrobp.2016.04.027. Epub May 7, 2016.

Menden, et al. Machine learning prediction of cancer cell sensitivity to drugs based on genomic and chemical properties. PLoS One. Apr. 30, 2013;8(4): e61318. doi: 10.1371/journal.pone.0061318. Print 2013.

Michot, et al. Immune-related adverse events with immune checkpoint blockade: a comprehensive review. Eur J Cancer. Feb. 2016;54:139-148. doi: 10.1016/j.ejca.2015.11.016. Epub Jan. 5, 2016.

Rahmani, et al. BayesCCE: a Bayesian framework for estimating cell-type composition from DNA methylation without the need for methylation reference. Genome Biol 19, 141 (2018). https://doi.org/10.1186/s13059-018-1513-2 (18 pages).

Rodríguez-Paredes, et al. Cancer epigenetics reaches mainstream oncology. Nat Med. Mar. 2011;17(3):330-339. doi: 10.1038/nm.2305.

Ruan, et al. Role of hypoxia in the hallmarks of human cancer. J Cell Biochem. Aug. 15, 2009;107(6):1053-1062. doi: 10.1002/jcb.22214.

Santos et al. Prognostic value of FLT3 mutations among different cytogenetic subgroups in acute myeloid leukemia. JNCI 117(10): 2145-2155. Year: 2011.

Templeton, et al. Prognostic role of neutrophil-to-lymphocyte ratio in solid tumors: a systematic review and meta-analysis. J Natl Cancer Inst. May 29, 2014;106(6):dju124. doi: 10.1093/jnci/dju124. Print Jun. 2014.

Teschendorff, et al. A comparison of reference-based algorithms for correcting cell-type heterogeneity in Epigenome-Wide Association Studies. BMC Bioinformatics. Feb. 13, 2017;18(1):105. doi: 10.1186/s12859-017-1511-5.

Thienpont, et al. Tumor hypoxia causes DNA hypermethylation by reducing TET activity. Nature. Sep. 1, 2016; 537(7618): 63-68. Published online Aug. 17, 2016. doi: 10.1038/nature19081.

Thierry AR, et al. Origins, structures, and functions of circulating DNA in oncology. Cancer and Metastasis Reviews. vol. 35, 3 (2016): 30 Pages.

Titus, et al. Cell-type deconvolution from DNA methylation: a review of recent applications. Hum Mol Genet. Oct. 1, 2017;26(R2):R216-R224. doi: 10.1093/hmg/ddx275.

Toustrup, et al. Gene expression classifier predicts for hypoxic modification of radiotherapy with nimorazole in squamous cell carcinomas of the head and neck. Radiother Oncol. Jan. 2012;102(1):122-129. doi: 10.1016/j.radonc.2011.09.010. Epub Oct. 11, 2011.

Travis WD., Pathology of lung cancer, Clin Chest Med., Dec. 2011;32(4):669-92. doi:10.1016/j.ccm.2011.08.005. PMID: 22054879.

U.S. Appl. No. 16/760,522 Office Action dated Mar. 23, 2023.

U.S. Appl. No. 16/760,522 Office Action dated Oct. 6, 2023.

U.S. Appl. No. 18/061,273 Office Action dated Nov. 30, 2023.

Wang et al. DNA methylation signatures in circulating cell-free DNA as biomarkers for the early detection of cancer. Science China. 2017, vol. 60, No. 4: 356-362.

Warton, et al. Methylated circulating tumor DNA in blood: power in cancer prognosis and response. Endocr Relat Cancer. Mar. 2016;23(3):R157-R171. doi: 10.1530/ERC-15-0369. Epub Jan. 13, 2016.

Wiencke, et al. Immunomethylomic approach to explore the blood neutrophil lymphocyte ratio (NLR) in glioma survival. Clin Epigenetics. Feb. 2, 2017;9:10. doi: 10.1186/s13148-017-0316-8. eCollection 2017.

Xia, et al. Recent advances in hypoxia-inducible factor (HIF)-1 inhibitors. Eur J Med Chem. Mar. 2012;49:24-40. doi: 10.1016/j.ejmech.2012.01.033. Epub Jan. 24, 2012.

(56) References Cited

OTHER PUBLICATIONS

Zhou et al. Alterations of biomarker profiles after neoadjuvant chemotherapy in breast cancer: tumor heterogeneity should be taken into consideration. Oncotarget 6(34): 36894-36902. 2015.
Zou, et al. Epigenome-wide association studies without the need for cell-type composition. Nat Methods. Mar. 2014;11(3):309-11. doi: 10.1038/nmeth.2815. Epub Jan. 26, 2014.

* cited by examiner

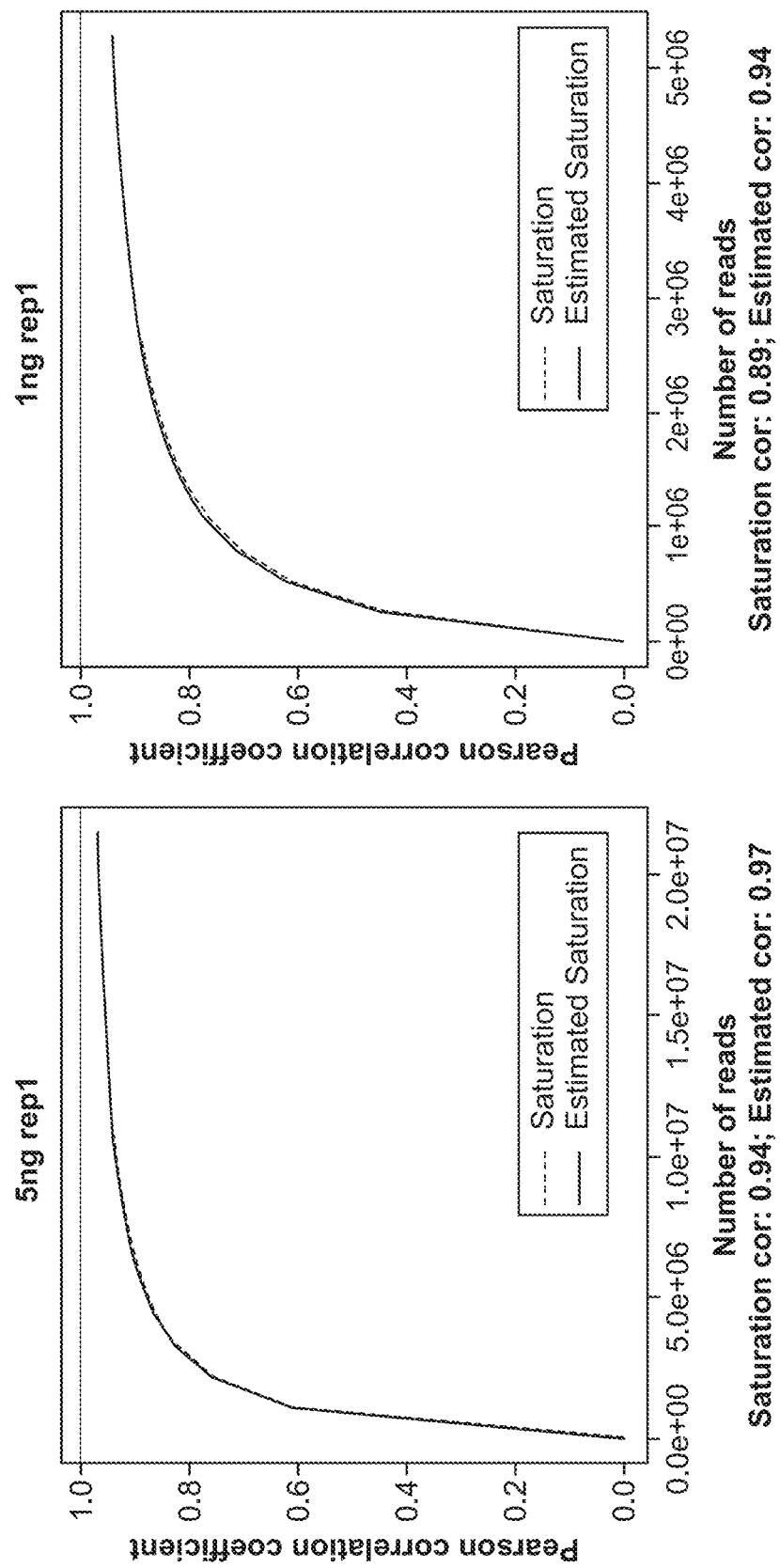
FIG. 6A (Cont. 1)

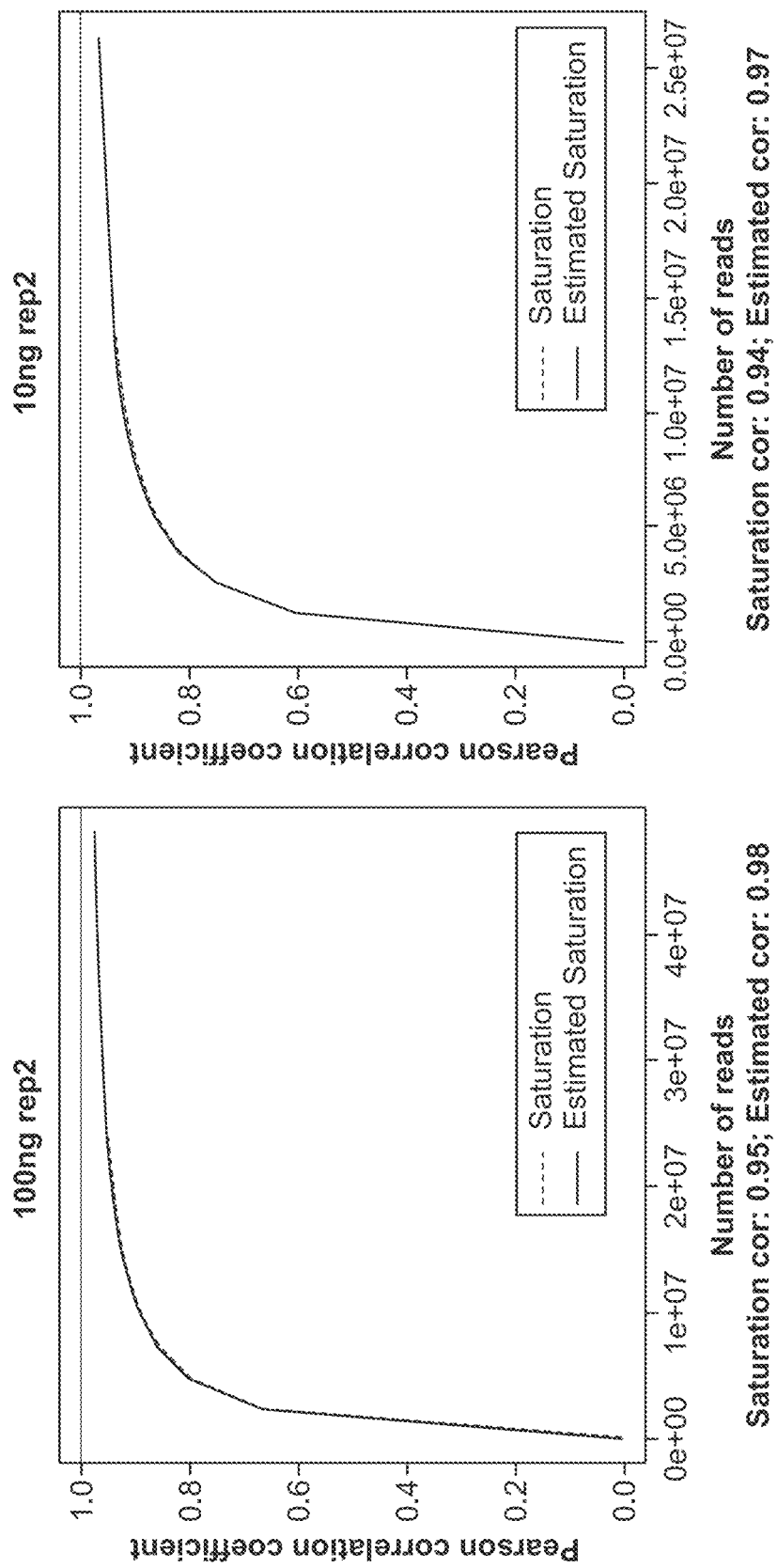
FIG. 6A (Cont. 2)

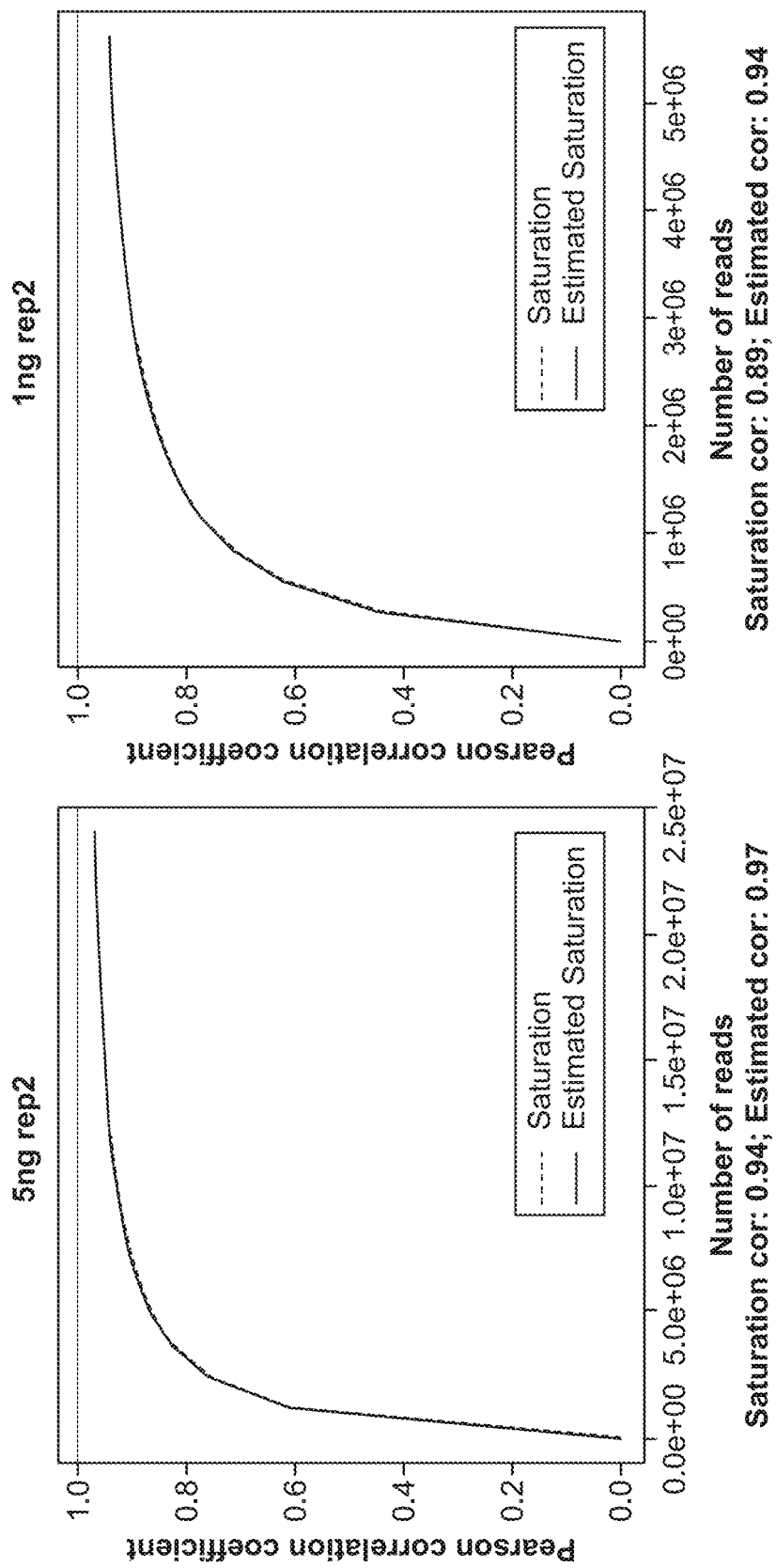
FIG. 6A (Cont. 3)

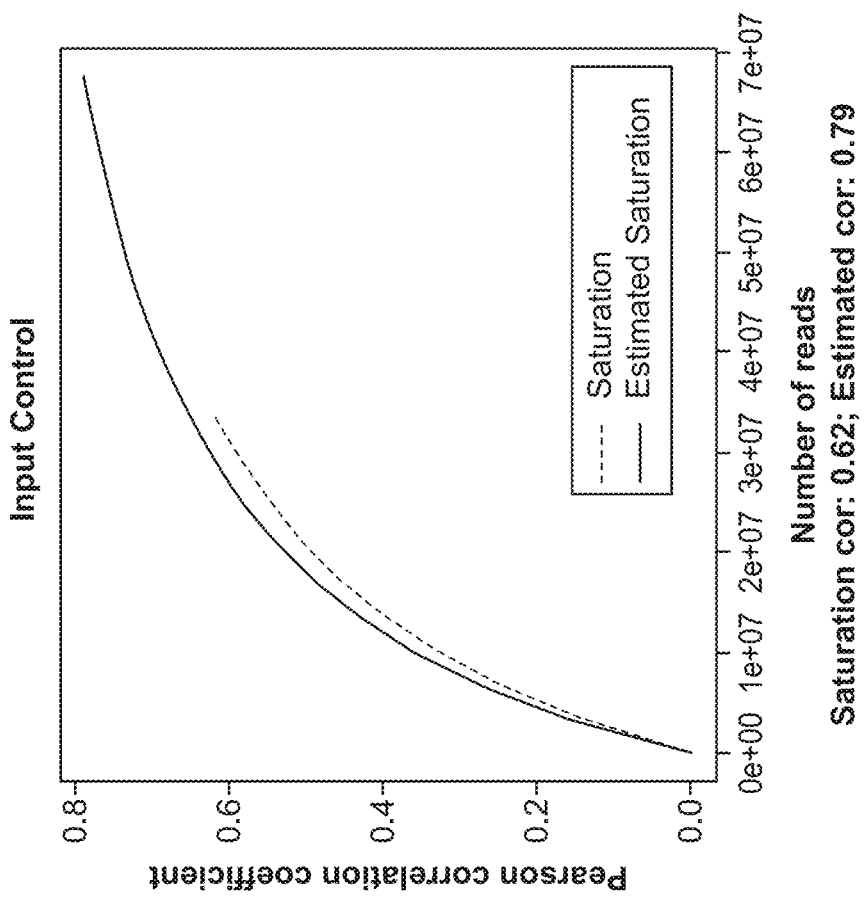
FIG. 6A (Cont. 4)

CANCER DETECTION AND CLASSIFICATION USING METHYLOME ANALYSIS

RELATED APPLICATIONS

This application is a National Stage Entry of International Application No. PCT/CA2018/00141filed Jul. 11, 2018, which claims priority to U.S. Provisional Patent Application No. 62/531,527 filed Jul. 12, 2017, which are all hereby incorporated by reference.

FIELD OF THE INVENTION

The invention relates to cancer detection and classification and more particularly to the use of methylome analysis for the same.

BACKGROUND OF THE INVENTION

The use of circulating cell-free DNA (cfDNA) as a source of biomarkers is rapidly gaining momentum in oncology[1]. Use of DNA methylation mapping of cfDNA as a biomarker could have a significant impact in the field of liquid biopsy, as it could allow for the identification of the tissue-of-origin [2], allow for cancer type and subtype classification, and stratify cancer patients in a minimally invasive fashion[3]. Furthermore, using genome-wide DNA methylation mapping of cfDNA could overcome a critical sensitivity problem in detecting circulating tumor DNA (ctDNA) in patients with early-stage cancer with no radiographic evidence of disease. Existing ctDNA detection methods are based on sequencing mutations and have limited sensitivity in part due to the limited number of recurrent mutations available to distinguish between tumor and normal circulating cfDNA[4, 5]. On the other hand, genome-wide DNA methylation mapping leverages large numbers of epigenetic alterations that may be used to distinguish circulating tumor DNA (ctDNA) from normal circulating cell-free DNA (cfDNA). For example, some tumor types, such as ependymomas, can have extensive DNA methylation aberrations without any significant recurrent somatic mutations[6].

Certain methods of capturing cell-free methylated DNA are described in WO 2017/190215, which is incorporated by reference.

SUMMARY OF THE INVENTION

In an aspect, there is provided a method of detecting the presence of DNA from cancer cells in a subject comprising: providing a sample of cell-free DNA from a subject; subjecting the sample to library preparation to permit subsequent sequencing of the cell-free methylated DNA; adding a first amount of filler DNA to the sample, wherein at least a portion of the filler DNA is methylated, then optionally denaturing the sample; capturing cell-free methylated DNA using a binder selective for methylated polynucleotides; sequencing the captured cell-free methylated DNA; comparing the sequences of the captured cell-free methylated DNA to control cell-free methylated DNAs sequences from healthy and cancerous individuals; identifying the presence of DNA from cancer cells if there is a statistically significant similarity between one or more sequences of the captured cell-free methylated DNA and cell-free methylated DNAs sequences from cancerous individuals.

In an aspect, there is provided a method of detecting the presence of DNA from cancer cells and identifying a cancer subtype, the method comprising: receiving sequencing data of cell-free methylated DNA from a subject sample; comparing the sequences of the captured cell-free methylated DNA to control cell-free methylated DNAs sequences from healthy and cancerous individuals; identifying the presence of DNA from cancer cells if there is a statistically significant similarity between one or more sequences of the captured cell-free methylated DNA and cell-free methylated DNAs sequences from cancerous individuals; and if DNA from cancer cells is identified, further identifying the cancer cell tissue of origin and cancer subtype based on the comparison.

In an aspect, there is provided a computer-implemented method of detecting the presence of DNA from cancer cells and identifying a cancer subtype, the method comprising: receiving, at least one processor, sequencing data of cell-free methylated DNA from a subject sample; comparing, at the at least one processor, the sequences of the captured cell-free methylated DNA to control cell-free methylated DNAs sequences from healthy and cancerous individuals; identifying, at the at least one processor, the presence of DNA from cancer cells if there is a statistically significant similarity between one or more sequences of the captured cell-free methylated DNA and cell-free methylated DNA sequences from cancerous individuals and if DNA from cancer cells is identified, further identifying the cancer cell tissue of origin and cancer subtype based on the comparison.

In an aspect, there is provided a computer program product for use in conjunction with a general-purpose computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided a computer readable medium having stored thereon a data structure for storing the computer program product described herein.

In an aspect, there is provided a device for detecting the presence of DNA from cancer cells and identifying a cancer subtype, the device comprising: at least one processor; and electronic memory in communication with the at one processor, the electronic memory storing processor-executable code that, when executed at the at least one processor, causes the at least one processor to: receive sequencing data of cell-free methylated DNA from a subject sample; compare the sequences of the captured cell-free methylated DNA to control cell-free methylated DNAs sequences from healthy and cancerous individuals; identify the presence of DNA from cancer cells if there is a statistically significant similarity between one or more sequences of the captured cell-free methylated DNA and cell-free methylated DNA sequences from cancerous individuals and if DNA from cancer cells is identified, further identify the cancer cell tissue of origin and cancer subtype based on the comparison.

In an aspect, there is provided a method of detecting the presence of DNA from cancer cells and determining the location of the cancer from which the cancer cells arose from two or more possible organs, the method comprising: providing a sample of cell-free DNA from a subject; capturing cell-free methylated DNA from said sample, using a binder selective for methylated polynucleotides; sequencing the captured cell-free methylated DNA; comparing the sequence patterns of the captured cell-free methylated DNA to DNAs sequence patterns of two or more population(s) of control individuals, each of said two or more populations having localized cancer in a different organ; determining as to which organ the cancer cells arose on the basis of a statistically significant similarity between the pattern of methylation of the cell-free DNA and one of said two or more populations.

BRIEF DESCRIPTION OF FIGURES

These and other features of the preferred embodiments of the invention will become more apparent in the following detailed description in which reference is made to the appended drawings wherein.

DETAILED DESCRIPTION

Figure 1A:
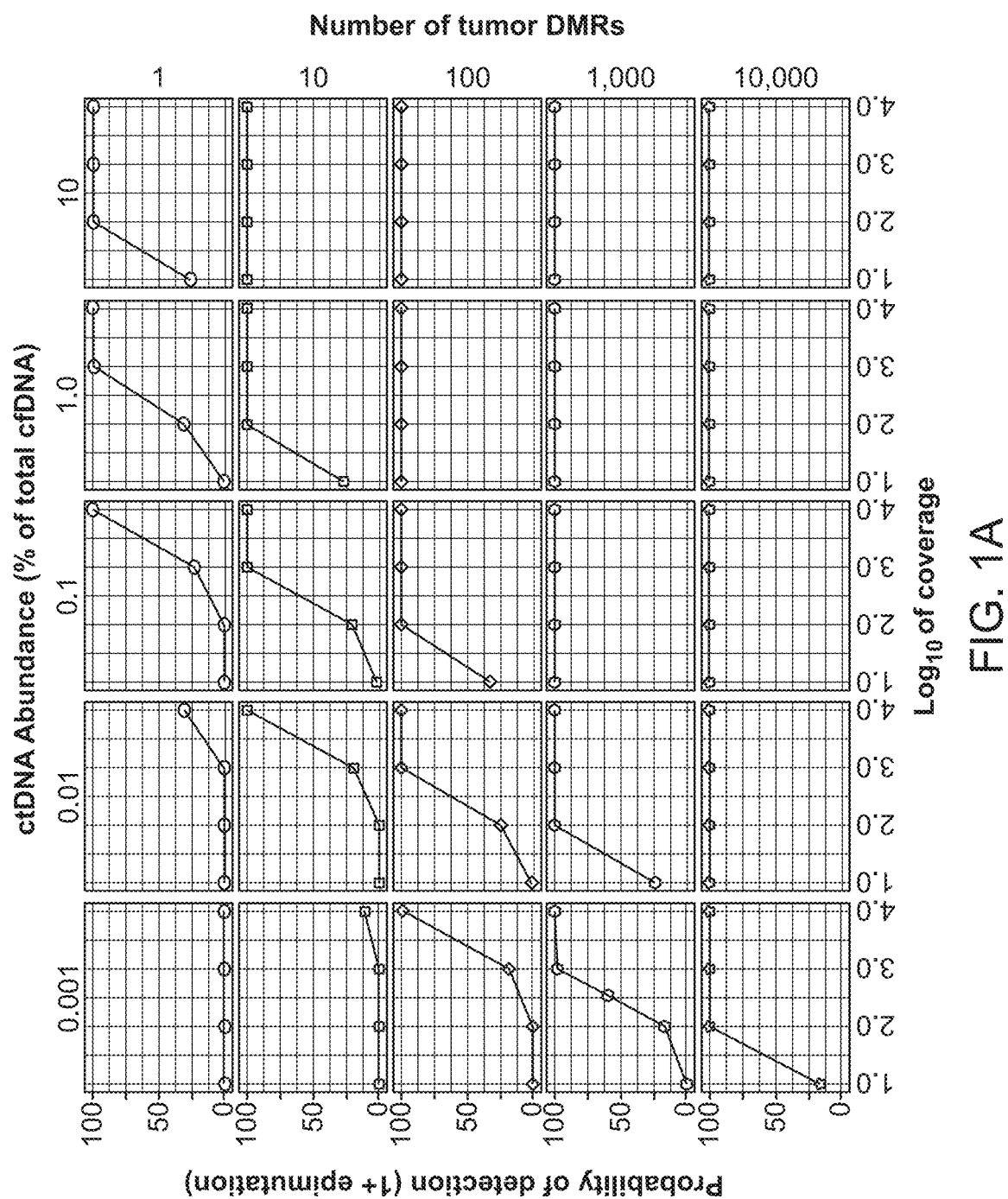
FIG. 1 shows methylome analysis of cfDNA is a highly sensitive approach to enrich and detect ctDNA in low amounts of input DNA. A) Computer Simulation of the probability to detect at least one epimutation as a function of the concentration of ctDNA (columns), number of DMRs being investigated (rows), and the sequencing depth (x-axis). B) Genome-wide Pearson correlation between DNA methylation signal for 1 to 100 ng of input DNA from HCT116 cell line fragmented to mimic plasma cfDNA. Each concentration has two biological replicates. C) DNA methylation profile obtained from cfMeDIP-seq from different concentrations of input DNA from HCT116 (Green Tracks) plus RRBS (Reduced Representation Bisulfite Sequencing) HCT116 data obtained from ENCODE (ENCSR000DFS) and WGBS (Whole-Genome Bisulfite Sequencing) HCT116 data obtained from GEO (GSM1465024). For the heatmap (RRBS track), yellow means methylated, blue means unmethylated and gray means no coverage. D-E) Serial dilution of the CRC cell line HCT116 into the Multiple Myeloma (MM) cell line MM1.S. cfMeDIP-seq was performed in pure HCT116 DNA (100% CRC), pure MM1.S DNA (100% MM) and 10%, 1%, 0.1%, 0.01%, and 0.001% CRC DNA diluted into MM DNA. All DNA was fragmented to mimic plasma cfDNA. We observed an almost perfect linear correlation ($r^2$=0.99, $p<0.0001$) between the observed versus expected (D) numbers of DMRs and (E) the DNA methylation signal (in RPKM) within those DMRs. F) In the same dilution series, known somatic mutations are only detectable at 1/100 allele fraction by ultra-deep (>10,000×) targeted sequencing, above the background sequencer and polymerase error rate. Shown are the fractions of reads containing each base or an insertion/deletion at the site of each mutation in the CRC cell line. G) Frequency of ctDNA (human) as a percentage of total cfDNA (human+mice) in the plasma of mice harboring patient-derived xenograft (PDX) from two colorectal cancer patients.

In the following description, numerous specific details are set forth to provide a thorough understanding of the invention. However, it is understood that the invention may be practiced without these specific details.

DNA methylation profiles are cell-type specific and are disrupted in cancer. Using a robust and sensitive method designed for methylome analysis of minute amounts of circulating cell-free DNA (cfDNA), we identified thousands of Differentially Methylated Regions (DMRs) that distinguish multiple tumor types from each other and from healthy individuals. Methylome analysis of cfDNA is highly sensitive and suitable for detecting circulating tumor DNA (ctDNA) in early stage patients. A machine-learning derived classifier using cfDNA methylomes was able to correctly classify 196 plasma samples from patients with 5 cancer types and healthy donors based on cross-validation. In an independent validation, using the same DMRs identified in the plasma cfDNA, the classifier was able to correctly classify AML, lung cancer, and healthy donors, as well as both early and late stage lung cancer. Therefore, methylome analysis of cfDNA can be used for non-invasive early stage detection of ctDNA and robustly classify cancer types.

In an aspect, there is provided a method of detecting the presence of DNA from cancer cells in a subject comprising: providing a sample of cell-free DNA from a subject; subjecting the sample to library preparation to permit subsequent sequencing of the cell-free methylated DNA; adding a first amount of filler DNA to the sample, wherein at least a portion of the filler DNA is methylated, then optionally denaturing the sample; capturing cell-free methylated DNA using a binder selective for methylated polynucleotides; sequencing the captured cell-free methylated DNA; comparing the sequences of the captured cell-free methylated DNA to control cell-free methylated DNAs sequences from healthy and cancerous individuals; identifying the presence of DNA from cancer cells if there is a statistically significant similarity between one or more sequences of the captured cell-free methylated DNA and cell-free methylated DNAs sequences from cancerous individuals.

Applicant's co-owned applications U.S. Provisional Patent Application No. 62/331,070 filed on May 3, 2016 and International Patent Application No. PCT/CA2017/000108 filed on May 3, 2017 describe method for capturing cell-free methylated DNA and are incorporated herein by reference.

Cancer has been traditionally classified by tissue of origin—for instance, colorectal cancer, breast cancer, lung cancer, etc. In the modern practice of clinical oncology, it is becoming increasingly important to be able to distinguish subtypes of cancer by various molecular, developmental, and functional underpinnings. Therapeutic decisions often hinge on the precise subtype of cancer, and it may be necessary for clinicians to identify the subtype prior to initiation of therapy. Examples of cancer subtyping that may influence therapeutic decisions include (but are not limited to) stage (e.g., early stage lung cancer treated with surgery vs late stage lung cancer treated with chemotherapy), histology (e.g., small cell carcinoma vs adenocarcinoma vs squamous cell carcinoma in lung cancer), gene expression pattern or transcription factor activity (e.g., ER status in breast cancer), copy number aberrations (e.g., HER2 status in breast cancer), specific rearrangements (e.g., FLT3 in AML), specific gene point mutational status (e.g., IDH gene point mutations), and DNA methylation patterns (e.g., MGMT gene promoter methylation in brain cancer).

The methods described herein are applicable to a wide variety of cancers, including but not limited to adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, penile cancer, pituitary tumors, prostate cancer, retinoblastoma, rhabdomyosarcoma, salivary gland cancer, sarcoma—adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, wilms tumor.

Various sequencing techniques are known to the person skilled in the art, such as polymerase chain reaction (PCR) followed by Sanger sequencing. Also available are next-generation sequencing (NGS) techniques, also known as high-throughput sequencing, which includes various sequencing technologies including: Illumine (Solexa) sequencing, Roche 454 sequencing, Ion torrent: Proton/PGM sequencing, SOLiD sequencing. NGS allow for the sequencing of DNA and RNA much more quickly and cheaply than the previously used Sanger sequencing. In some embodiments, said sequencing is optimized for short read sequencing.

The term "subject" as used herein refers to any member of the animal kingdom, preferably a human being and most preferably a human being that has, has had, or is suspected of having prostate cancer.

Cell-free methylated DNA is DNA that is circulating freely in the blood stream, and are methylated at various known regions of the DNA. Samples, for example, plasma samples can be taken to analyze cell-free methylated DNA. Accordingly, in some embodiments, the sample is the subject's blood or plasma.

As used herein, "library preparation" includes list end-repair, A-tailing, adapter ligation, or any other preparation performed on the cell free DNA to permit subsequent sequencing of DNA.

As used herein, "filler DNA" can be noncoding DNA or it can consist of amplicons.

DNA samples may be denatured, for example, using sufficient heat.

In some embodiments, the comparison step is based on fit using a statistical classifier. Statistical classifiers using DNA methylation data can be used for assigning a sample to a particular disease state, such as cancer type or subtype. For the purpose of cancer type or subtype classification, a classifier would consist of one or more DNA methylation variables (i.e., features) within a statistical model, and the output of the statistical model would have one or more threshold values to distinguish between distinct disease states. The particular feature(s) and threshold value(s) that are used in the statistical classifier can be derived from prior knowledge of the cancer types or subtypes, from prior knowledge of the features that are likely to be most informative, from machine learning, or from a combination of two or more of these approaches.

In some embodiments, the classifier is machine learning-derived. Preferably, the classifier is an elastic net classifier, lasso, support vector machine, random forest, or neural network.

The genomic space that is analyzed can be genome-wide, or preferably restricted to regulatory regions (i.e., FANTOM5 enhancers, CpG Islands, CpG shores and CpG Shelves).

Preferably, the percentage of spike-in methylated DNA recovered is included as a covariate to control for pulldown efficiency variation.

For a classifier capable of distinguishing multiple cancer types (or subtypes) from one another, the classifier would preferably consist of differentially methylated regions from pairwise comparisons of each type (or subtype) of interest.

In some embodiments, the control cell-free methylated DNAs sequences from healthy and cancerous individuals are comprised in a database of Differentially Methylated Regions (DMRs) between healthy and cancerous individuals.

In some embodiments, the control cell-free methylated DNA sequences from healthy and cancerous individuals are limited to those control cell-free methylated DNA sequences which are differentially methylated as between healthy and cancerous individuals in DNA derived from cell-free DNA from bodily fluids, such as from blood serum, cerebral spinal fluid, urine stool, sputum, pleural fluid, ascites, tears, sweat, pap smear fluid, endoscopy brushings fluid, . . . etc., preferably from blood plasma.

In some embodiments, the sample has less than 100 ng, 75 ng, or 50 ng of cell-free DNA.

In some embodiments, the first amount of filler DNA comprises about 5%, 10%, 15%, 20%, 30%, 40%, 50%, 60%, 70%, 80%, 90%, or 100% methylated filler DNA with remainder being unmethylated filler DNA, and preferably between 5% and 50%, between 10%-40%, or between 15%-30% methylated filler DNA.

In some embodiments, the first amount of filler DNA is from 20 ng to 100 ng, preferably 30 ng to 100 ng, more preferably 50 ng to 100 ng.

In some embodiments, the cell-free DNA from the sample and the first amount of filler DNA together comprises at least 50 ng of total DNA, preferably at least 100 ng of total DNA.

In some embodiments, the filler DNA is 50 bp to 800 bp long, preferably 100 bp to 600 bp long, and more preferably 200 bp to 600 bp long.

In some embodiments, the filler DNA is double stranded. The filler DNA is double stranded. For example, the filler DNA can be junk DNA. The filler DNA may also be endogenous or exogenous DNA. For example, the filler DNA is non-human DNA, and in preferred embodiments, λ DNA. As used herein, "λ DNA" refers to *Enterobacteria phage* λ DNA. In some embodiments, the filler DNA has no alignment to human DNA.

In some embodiments, the binder is a protein comprising a Methyl-CpG-binding domain. One such exemplary protein is MBD2 protein. As used herein, "Methyl-CpG-binding domain (MBD)" refers to certain domains of proteins and enzymes that is approximately 70 residues long and binds to DNA that contains one or more symmetrically methylated CpGs. The MBD of MeCP2, MBD1, MBD2, MBD4 and BAZ2 mediates binding to DNA, and in cases of MeCP2, MBD1 and MBD2, preferentially to methylated CpG. Human proteins MECP2, MBD1, MBD2, MBD3, and MBD4 comprise a family of nuclear proteins related by the presence in each of a methyl-CpG-binding domain (MBD). Each of these proteins, with the exception of MBD3, is capable of binding specifically to methylated DNA.

In other embodiments, the binder is an antibody and capturing cell-free methylated DNA comprises immunoprecipitating the cell-free methylated DNA using the antibody.

As used herein, "immunoprecipitation" refers a technique of precipitating an antigen (such as polypeptides and nucleotides) out of solution using an antibody that specifically binds to that particular antigen. This process can be used to isolate and concentrate a particular protein or DNA from a sample and requires that the antibody be coupled to a solid substrate at some point in the procedure. The solid substrate includes for examples beads, such as magnetic beads. Other types of beads and solid substrates are known in the art.

One exemplary antibody is 5-MeC antibody. For the immunoprecipitation procedure, in some embodiments at least 0.05 µg of the antibody is added to the sample; while in more preferred embodiments at least 0.16 µg of the antibody is added to the sample. To confirm the immunoprecipitation reaction, in some embodiments the method described herein further comprises the step of adding a second amount of control DNA to the sample.

In some embodiments, the method further comprises the step of adding a second amount of control DNA to the sample for confirming the immunoprecipitation reaction.

As used herein, the "control" may comprise both positive and negative control, or at least a positive control.

In some embodiments, the method further comprises the step of adding a second amount of control DNA to the sample for confirming the capture of cell-free methylated DNA.

In some embodiments, identifying the presence of DNA from cancer cells further includes identifying the cancer cell tissue of origin.

In some instances, tumor tissue sampling may be challenging or carry significant risks, in which case diagnosing and/or subtyping the cancer without the need for tumor tissue sampling may be desired. For example, lung tumor tissue sampling may require invasive procedures such as mediastinoscopy, thoracotomy, or percutaneous needle biopsy; these procedures may result in a need for hospitalization, chest tube, mechanical ventilation, antibiotics, or other medical interventions. Some individuals may not undergo the invasive procedures needed for tumor tissue sampling either because of medical comorbidities or due to preference. In some instances, the actual procedure for tumor tissue procurement may depend on the suspected cancer subtype. In other instances, cancer subtype may evolve over time within the same individual; serial assessment with invasive tumor tissue sampling procedures is often impractical and not well tolerated by patients. Thus, non-invasive cancer subtyping via blood test could have many advantageous applications in the practice of clinical oncology.

Accordingly, in some embodiments, identifying the cancer cell tissue of origin further includes identifying a cancer subtype. Preferably, the cancer subtype differentiates the cancer based on stage (e.g., early stage lung cancer treated with surgery vs late stage lung cancer treated with chemotherapy), histology (e.g., small cell carcinoma vs adenocarcinoma vs squamous cell carcinoma in lung cancer), gene expression pattern or transcription factor activity (e.g., ER status in breast cancer), copy number aberrations (e.g., HER2 status in breast cancer), specific rearrangements (e.g., FLT3 in AML), specific gene point mutational status (e.g., IDH gene point mutations), and DNA methylation patterns (e.g., MGMT gene promoter methylation in brain cancer).

In some embodiments, comparison in step (f) is carried out genome-wide.

In other embodiments, the comparison in step (f) is restricted from genome-wide to specific regulatory regions, such as, but not limited to, FANTOM5 enhancers, CpG Islands, CpG shores, CpG Shelves, or any combination of the foregoing.

In some embodiments, certain steps are carried out by a computer processor.

In an aspect, there is provided a method of detecting the presence of DNA from cancer cells and identifying a cancer subtype, the method comprising: receiving sequencing data of cell-free methylated DNA from a subject sample; comparing the sequences of the captured cell-free methylated DNA to control cell-free methylated DNAs sequences from healthy and cancerous individuals; identifying the presence of DNA from cancer cells if there is a statistically significant similarity between one or more sequences of the captured cell-free methylated DNA and cell-free methylated DNAs sequences from cancerous individuals; and if DNA from cancer cells is identified, further identifying the cancer cell tissue of origin and cancer subtype based on the comparison step.

In an aspect, there is provided a method of detecting the presence of DNA from cancer cells and determining the location of the cancer from which the cancer cells arose from two or more possible organs, the method comprising: providing a sample of cell-free DNA from a subject; capturing cell-free methylated DNA from said sample, using a binder selective for methylated polynucleotides; sequencing the captured cell-free methylated DNA; comparing the sequence patterns of the captured cell-free methylated DNA to DNAs sequence patterns of two or more population(s) of control individuals, each of said two or more populations having localized cancer in a different organ; determining as to which organ the cancer cells arose on the basis of a statistically significant similarity between the pattern of methylation of the cell-free DNA and one of said two or more populations.

Figure 5:
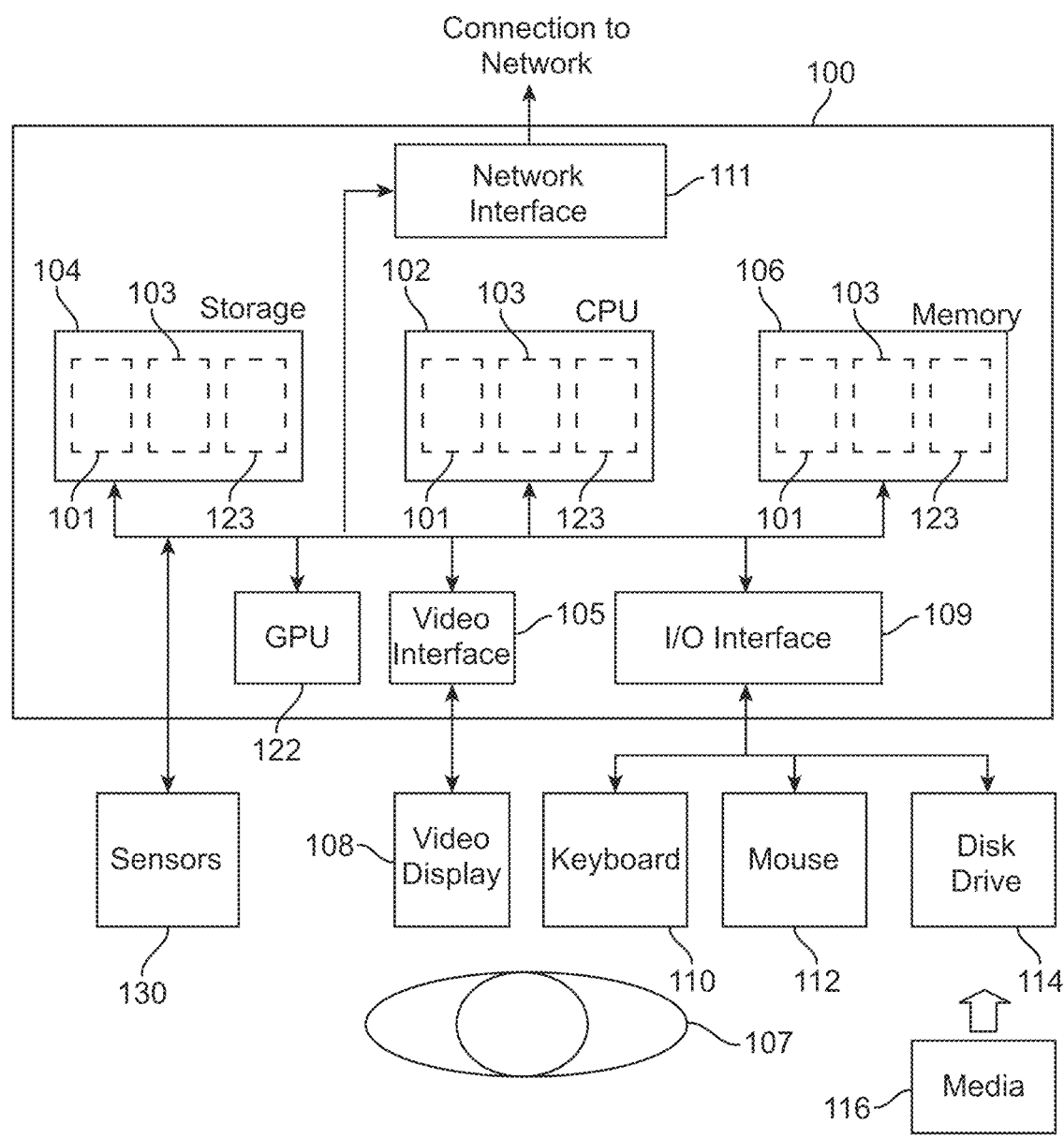
FIG. 5 shows a suitable configured computer device, and associated communications networks, devices, software and firmware to provide a platform for enabling one or more embodiments as described herein.

The present system and method may be practiced in various embodiments. A suitably configured computer device, and associated communications networks, devices, software and firmware may provide a platform for enabling one or more embodiments as described above. By way of example, FIG. 5 shows a generic computer device 100 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 100 may further include a graphics processing unit (GPU) 122 which is operatively connected to CPU 102 and to memory 106 to offload intensive image processing calculations from CPU 102 and run these calculations in parallel with CPU 102. An operator 107 may interact with the computer device 100 using a video display 108 connected by a video interface 105, and various input/output devices such as a keyboard 115, mouse 112, and disk drive or solid state drive 114 connected by an I/O interface 109. In known manner, the mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 100 may form part of a network via a network interface 111, allowing the computer device 100 to communicate with other suitably configured data processing systems (not shown). One or more different types of sensors 135 may be used to receive input from various sources.

The present system and method may be practiced on virtually any manner of computer device including a desktop computer, laptop computer, tablet computer or wireless handheld. The present system and method may also be implemented as a computer-readable/useable medium that includes computer program code to enable one or more computer devices to implement each of the various process steps in a method in accordance with the present invention. In case of more than computer devices performing the entire operation, the computer devices are networked to distribute the various steps of the operation. It is understood that the terms computer-readable medium or computer useable medium comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

In an aspect, there is provided a computer-implemented method of detecting the presence of DNA from cancer cells and identifying a cancer subtype, the method comprising: receiving, at least one processor, sequencing data of cell-free methylated DNA from a subject sample; comparing, at the at least one processor, the sequences of the captured cell-free methylated DNA to control cell-free methylated DNAs sequences from healthy and cancerous individuals; identifying, at the at least one processor, the presence of DNA from cancer cells if there is a statistically significant similarity between one or more sequences of the captured cell-free methylated DNA and cell-free methylated DNAs sequences from cancerous individuals and if DNA from cancer cells is identified, further identifying the cancer cell tissue of origin and cancer subtype based on the comparison step;

In an aspect, there is provided a computer program product for use in conjunction with a general-purpose computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided a computer readable medium having stored thereon a data structure for storing the computer program product described herein.

In an aspect, there is provided a device for detecting the presence of DNA from cancer cells and identifying a cancer subtype, the device comprising: at least one processor; and electronic memory in communication with the at one processor, the electronic memory storing processor-executable code that, when executed at the at least one processor, causes the at least one processor to: receive sequencing data of cell-free methylated DNA from a subject sample; compare the sequences of the captured cell-free methylated DNA to control cell-free methylated DNAs sequences from healthy and cancerous individuals; identify the presence of DNA from cancer cells if there is a statistically significant similarity between one or more sequences of the captured cell-free methylated DNA and cell-free methylated DNAs sequences from cancerous individuals and if DNA from cancer cells from is identified, further identify the cancer cell tissue of origin and cancer subtype based on the comparison step.

As used herein, "processor" may be any type of processor, such as, for example, any type of general-purpose microprocessor or microcontroller (e.g., an Intel™ x86, PowerPC™, ARM™ processor, or the like), a digital signal processing (DSP) processor, an integrated circuit, a field programmable gate array (FPGA), or any combination thereof.

As used herein "memory" may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like. Portions of memory 102 may be organized using a conventional filesystem, controlled and administered by an operating system governing overall operation of a device.

As used herein, "computer readable storage medium" (also referred to as a machine-readable medium, a processor-readable medium, or a computer usable medium having a computer-readable program code embodied therein) is a medium capable of storing data in a format readable by a computer or machine. The machine-readable medium can be any suitable tangible, non-transitory medium, including a magnetic, optical, or electrical storage medium including a diskette, compact disk read only memory (CD-ROM), memory device (volatile or non-volatile), or similar storage mechanism. The computer readable storage medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the computer readable storage medium. The instructions stored on the computer readable storage medium can be executed by a processor or other suitable processing device, and can interface with circuitry to perform the described tasks.

As used herein, "data structure" a particular way of organizing data in a computer so that it can be used efficiently. Data structures can implement one or more particular abstract data types (ADT), which specify the operations that can be performed on a data structure and the computational complexity of those operations. In comparison, a data structure is a concrete implementation of the specification provided by an ADT.

The advantages of the present invention are further illustrated by the following examples. The examples and their particular details set forth herein are presented for illustration only and should not be construed as a limitation on the claims of the present invention.

EXAMPLES

Methods and Materials
Donor Recruitment and Sample Acquisition
CRC, Breast cancer, and GBM samples were obtained from the University Health Network BioBank; AML samples were obtained from the University Health Network Leukemia BioBank; Lastly, healthy controls were recruited through the Family Medicine Centre at Mount Sinai Hospital (MSH) in Toronto, Canada. All samples collected with patient consent, were obtained with institutional approval from the Research Ethics Board, from University Health Network and Mount Sinai Hospital in Toronto, Canada.

Specimen Processing—cfDNA
EDTA and ACD plasma samples were obtained from the BioBanks and from the Family Medicine Centre at Mount Sinai Hospital (MSH) in Toronto, Canada. All samples were either stored at −80° C. or in vapour phase liquid nitrogen until use. Cell-free DNA was extracted from 0.5-3.5 ml of plasma using the QIAamp™ Circulating Nucleic Acid Kit (Qiagen). The extracted DNA was quantified through Qubit prior to use.

Specimen Processing—PDX cfDNA
Human colorectal tumor tissue obtained with patient consent from the University Health Network Biobank as approved by the Research Ethics Board at University Health Network, was digested to single cells using collagenase A. Single cells were subcutaneously injected into 4-6 week old NOD/SCID male mouse. Mice were euthanized by CO2 inhalation prior to blood collection by cardiac puncture and stored in EDTA tubes. From the collected blood samples, the plasma was isolated and stored at −80 C. Cell-free DNA was extracted from 0.3-0.7 ml of plasma using the QIAamp™ Circulating Nucleic Acid Kit (Qiagen). All animal work was carried out in compliance with the ethical regulations approved by the Animal Care Committee at University Health Network.

cfMeDIP-seq
A schematic representation of the cfMeDIP-seq protocol is shown in WO2017/190215. Prior to cfMeDIP, the DNA samples were subjected to library preparation using the Kapa® Hyper Prep Kit (Kapa Biosystems). The manufacturer protocol was followed with some modifications. Briefly, the DNA of interest was added to 0.2 mL PCR tube and subjected to end-repair and A-Tailing. Adapter ligation was followed using NEBNext adapter (from the NEBNext Multiplex Oligos for Illumina kit, New England Biolabs) at a final concentration of 0.181 µM, incubated at 20° C. for 20 mins and purified with AMPure™ XP beads. The eluted library was digested using the USER enzyme (New England Biolabs Canada) followed by purification with Qiagen MinElute® PCR Purification Kit prior to MeDIP.

The prepared libraries were combined with the pooled methylated/unmethylated PCR product to a final DNA amount of 100 ng and subjected to MeDIP using the protocol from Taiwo et al. 2012[7] with some modifications. Briefly, for MeDIP, the Diagenode™ MagMeDIP kit (Cat #CO2010021) was used following the manufacturer's protocol with some modifications. Briefly, for MeDIP, the Diagenode™ MagMeDIP kit (Cat #CO2010021) was used following the manufacturer's protocol with some modifications. After the addition of 0.3 ng of the control methylated and 0.3 ng of the control unmethylated *A. thaliana* DNA, the filler DNA (to complete the total amount of DNA [cfDNA+Filler+Controls] to 100 ng) and the buffers to the PCR tubes containing the adapter ligated DNA, the samples were heated to 95° C. for 10 mins, then immediately placed into an ice water bath for 10 mins. Each sample was partitioned into two 0.2 mL PCR tubes: one for the 10% input control and the other one for the sample to be subjected to immunoprecipitation. The included 5-mC monoclonal antibody 33D3 (Cat #C15200081) from the MagMeDIP kit was diluted 1:15 prior to generating the diluted antibody mix and added to the sample. Washed magnetic beads (following manufacturer instructions) were also added prior to incubation at 4° C. for 17 hours. The samples were purified using the Diagenode™ iPure Kit and eluted in 50 µL of Buffer C. The success of the reaction (QC1) was validated through qPCR to detect the presence of the spiked-in *A. thaliana* DNA, ensuring a % recovery of unmethylated spiked-in DNA <1% and the % specificity of the reaction >99% (as calculated by 1-[recovery of spiked-in unmethylated control DNA over recovery of spiked-in methylated control DNA]), prior to proceeding to the next step. The optimal number of cycles to amplify each library was determined through the use of qPCR, after which the samples were amplified using the KAPA® HiFi Hotstart Mastermix and the NEBNext multiplex oligos added to a final concentration of 0.3 µM. The PCR settings used to amplify the libraries were as follows: activation at 95° C. for 3 min, followed by predetermined cycles of 98° C. for 20 sec, 65° C. for 15 sec and 72° C. for 30 sec and a final extension of 72° C. for 1 min. The amplified libraries were purified using MinElute® PCR purification column and then gel size selected with 3% Nusieve™ GTG agarose gel to remove any adapter dimers. Prior to submission for sequencing, the fold enrichment of a methylated human DNA region (testis-specific H2B, TSH2B) and an unmethylated human DNA region (GAPDH promoter) was determined for the MeDIP-seq and cfMeDIP-seq libraries generated from the HCT116 cell line DNA sheared to mimic cell free DNA (Cell line obtained from ATCC, mycoplasma free). The final libraries were submitted for BioAnalyzer analysis prior to sequencing at the UHN Princess Margaret Genomic Centre on an Illumina® HiSeq 2000.

Ultra-Deep Targeted Sequencing for Point Mutation Detection

We used the QIAgen Circulating Nucleic Acid kit to isolate cell-free DNA from −20 mL of plasma (4-5×10 mL EDTA blood tubes) from patients with matched tumor tissue molecular profiling data generated prior to enrolment in early phase clinical trials at the Princess Margaret Cancer Centre. DNA was extracted from cell lines (dilution of CRC and MM cell lines) using the PureGene™ Gentra kit, fragmented to −180 bp using a Covaris™ sonicator, and larger size fragments excluded using Ampure™ beads to mimic the fragment size of cell-free DNA. DNA sequencing libraries were constructed from 83 ng of fragmented DNA using the KAPA® Hyper Prep Kit (Kapa Biosystems, Wilmington, MA) utilizing NEXTflex-96 DNA Barcode adapters (Bio Scientific, Austin, TX) adapters. To isolate DNA fragments containing known mutations, we designed biotinylated DNA capture probes (xGen Lockdown Custom Probes Mini Pool, Integrated DNA Technologies, Coralville, IA) targeting mutation hotspots from 48 genes tested by the clinical laboratory using the Illumina® TruSeq Amplicon Cancer Panel. The barcoded libraries were pooled and then applied the custom hybrid capture library following manufacturer's instructions (IDT® xGEN Lockdown protocol version 2.1). These fragments were sequenced to >10,000× read coverage using an Illumina® HiSeq 2000 instrument. Resulting reads were aligned using bwa-mem and mutations detected using samtools and muTect version 1.1.4.

Modelling Relationships Between Number of Tumor-Specific Features and Probability of Detection by Sequencing Depth We created 145,000 simulated genomes, with the proportion of cancer-specific methylated DMRs set to 0.001%, 0.01%, 0.1%, 1%, and 10% and consisting of 1, 10, 100, 1000 and 10000 independent DMRs respectively. We sampled 14,500 diploid genomes (representing 100 ng of DNA) from these original mixtures and further sampled 10, 100, 1000, and 10000 reads per locus to represent sequencing coverage at those depths. This process was repeated 100 times for each combination of coverage, abundance, and number of features. We estimated the frequency of successful detection of at least 1 DMR for each combination of parameters and plotted probability curves (FIG. 1A) to visually evaluate the influence of the number of features on the probability of successful detection conditional on sequencing depths.

Derivation of Tissue-Distinctive Features, Development of a Multi-Tissue Classifier and Validation in 450k Data cfDNA MeDIP profiles were quantified using the MEDIPS R package[8], converted to RPKMs, and afterwards transformed into log 2 counts-per-million. Subsequently, a linear model was fit using limma-trend[9] on a matrix of features that mapped to FANTOM5 enhancers, CpG Islands, CpG shores and CpG Shelves, with the percentage of spike-in methylated DNA recovered included as a covariate to control for pulldown efficiency variation. Pairwise contrasts were evaluated for each pair of tissue types and the top 150 and the bottom 150 DMRs were selected for elastic net classifier training and validation of cancer-type specificity. Performance metrics were derived by majority class votes on out-of-fold calls from the model with the highest Kappa value in cross-validation, a heuristic previously employed in Chakravarthy et alp[10].

Machine Learning Analyses for Evaluation of Classification Accuracy

Model Training and Evaluation on the Discovery Cohort

Figure 2A:
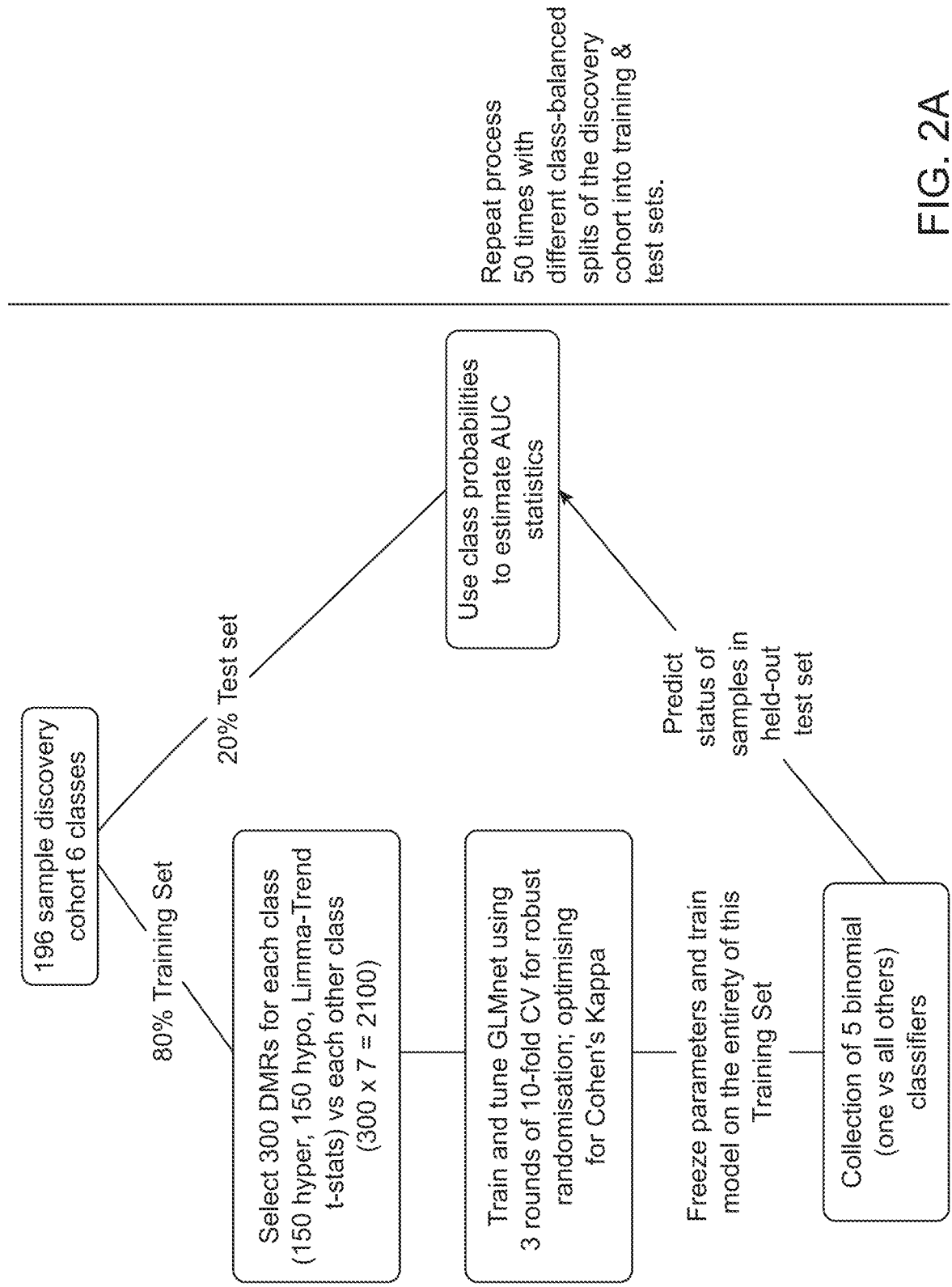
FIG. 2 shows the methylome analysis of plasma cfDNA allows tumor classification. A) Schematic demonstrating the approach of machine learning classifier construction for cancer classification. B) Heatmap of DMRs contained within the multi-class elastic net machine learning classifiers. The classifiers were trained on plasma DNA samples from healthy donors (n=24), lung cancer (n=25), breast cancer (n=25), colorectal cancer (n=23), acute myelogenous leukemia (AML) (n=28), and glioblasatoma multiforme (GBM) (n=71). Hierarchical clustering method: Ward. C) 2D visualizations by tSNE (t-Distributed Stochastic Neighbor Embedding) of the cancer-type associated DMRs identified in 10% or 25% of models. D) Performance metrics for the plasma cfDNA methylation-based multi-cancer classifier. Area under the receiver operator curve (auROC) shown on the y-axis for each cancer type and healthy donors following 50-fold generation of elastic net machine learning classifiers.

In order to evaluate the performance of cfMeDIP data in tumor classification without high computational cost, we reduced the initial set of possible candidate features to windows encompassing CpG Islands, shores, shelves and FANTOM5 enhancers (hereby labelled "regulatory features"), yielding a matrix of 196 samples and 505,027 features. We then used the caret R package to partition the discovery cohort data into 50 independent training and test sets in an 80%-20% manner (FIG. 2A). The splits were performed while class proportions across the discovery cohort were maintained. Then, we selected the top 300 DMRs by moderated t-statistic (150 hypermethylated, 150 hypomethylated) on the training data partition using limma-trend for each class versus other classes. A binomial GLMnet was then trained using these DMRs (up to 300 DMRs×7 other classes=2100 features) with the use of 3 iterations of 10-Fold Cross-Validation (CV) to optimize values of the mixing parameter (alpha, values=0, 0.2, 0.5, 0.8 and 1) and the penalty (lambda, values=0–0.05 in increments of 0.01) using Cohen's Kappa as the performance metric. For each training set, this yielded a collection of 6 one-class vs-other-classes binomial classifiers.

We then estimated classification performance on the held-out test set using the AUROC (area under the receiver operating characteristic curve). These estimates represent unbiased measures of classification, as the held-out test set samples were not used for either DMR pre-selection or GLMnet training and tuning. The 50 independent training and test sets also permitted for minimization of optimistic estimates due to training-set bias.

Model Evaluation on the Validation Cohort

For each validation cohort cfMeDIP sample, we estimated class probabilities for the AML, LUC and normal one-vs-all binomial classifiers trained on the 50 different training sets within the discovery cohort. The probabilities from the 50 models were averaged to produce a single score that was then used for AUROC estimation. We also evaluated if disease stage affected performance by estimating AUROC when either early (Stages I and II) or late stage LUC samples (Stages III and IV) were left out for the one-vs-all classifier.

Results and Discussion

We bioinformatically simulated mixtures with different proportions of ctDNA, from 0.001% to 10% (FIG. 1A, column facets). We also simulated scenarios where the ctDNA had 1, 10, 100, 1000, or 10000 DMRs (Differentially Methylated Regions) as compared to normal cfDNA (FIG. 1A, row facets). Reads were then sampled at varying sequencing depths at each locus (10×, 100×, 1000×, and 10000×) (FIG. 1A, x-axis). We found an increasing probability of detecting of at least 1 cancer-specific event (FIG. 1A) as the number of DMRs increased, even at low abundance of cancer ctDNA and shallow coverage.

Moreover, pan-cancer data from The Cancer Genome Atlas (TCGA) shows large numbers of DMRs between tumor and normal tissues across virtually all tumor types [11]. Therefore, these findings highlighted that an assay that successfully recovered cancer-specific DNA methylation alterations from ctDNA could serve as a very sensitive tool to detect, classify, and monitor malignant disease with low sequencing-associated costs.

However, genome-wide mapping of DNA methylation in plasma cfDNA is challenging due to the very low quantities and fragmentation of DNA in circulation[12]. As a result, previous efforts at methylation profiling of cfDNA has mainly been restricted to locus specific PCR-based assays[2, 3], such as an FDA approved SEPT9 methylation assay for colorectal cancer screening[13]. While recent efforts have been made to perform whole-genome bisulfite-sequencing of fragmented cfDNA[14-16], the low genome-wide abundance of CpGs is likely to reduce the amount of useful methylation-related information available from sequencing. Therefore, the main issues with WGBS on plasma DNA are the high cost, low efficiency, and DNA losses associated with the bisulfite conversion. On the other hand, a method that selectively enriches for CpG-rich features prone to methylation is likely to maximize the amount of useful information available per read, decrease the cost, and decrease the DNA losses.

A Genome-Wide Method Suitable for cfDNA Methylation Mapping

We developed a new method termed cfMeDIP-seq (cell-free Methylated DNA Immunoprecipitation and high-throughput sequencing) to perform genome-wide DNA methylation mapping using cell-free DNA. The cfMeDIP-seq method described here was developed through the modification of an existing low input MeDIP-seq protocol [7] that in our experience is very robust down to 100 ng of input DNA. However, the majority of plasma samples yield much less than 100 ng of DNA. To overcome this challenge, we added exogenous λ DNA (filler DNA) to the adapter-ligated cfDNA library in order to artificially inflate the amount of starting DNA to 100 ng. This minimizes the amount of non-specific binding by the antibody and also minimizes the amount of DNA lost due to binding to plasticware. The filler DNA consisted of amplicons similar in size to an adapter-ligated cfDNA library and was composed of unmethylated and in vitro methylated DNA at different CpG densities. The addition of this filler DNA also serves a practical use, as different patients will yield different amounts of cfDNA, allowing for the normalization of input DNA amount to 100 ng. This ensures that the downstream protocol remains exactly the same for all samples regardless of the amount of available cfDNA.

Figure 6A:
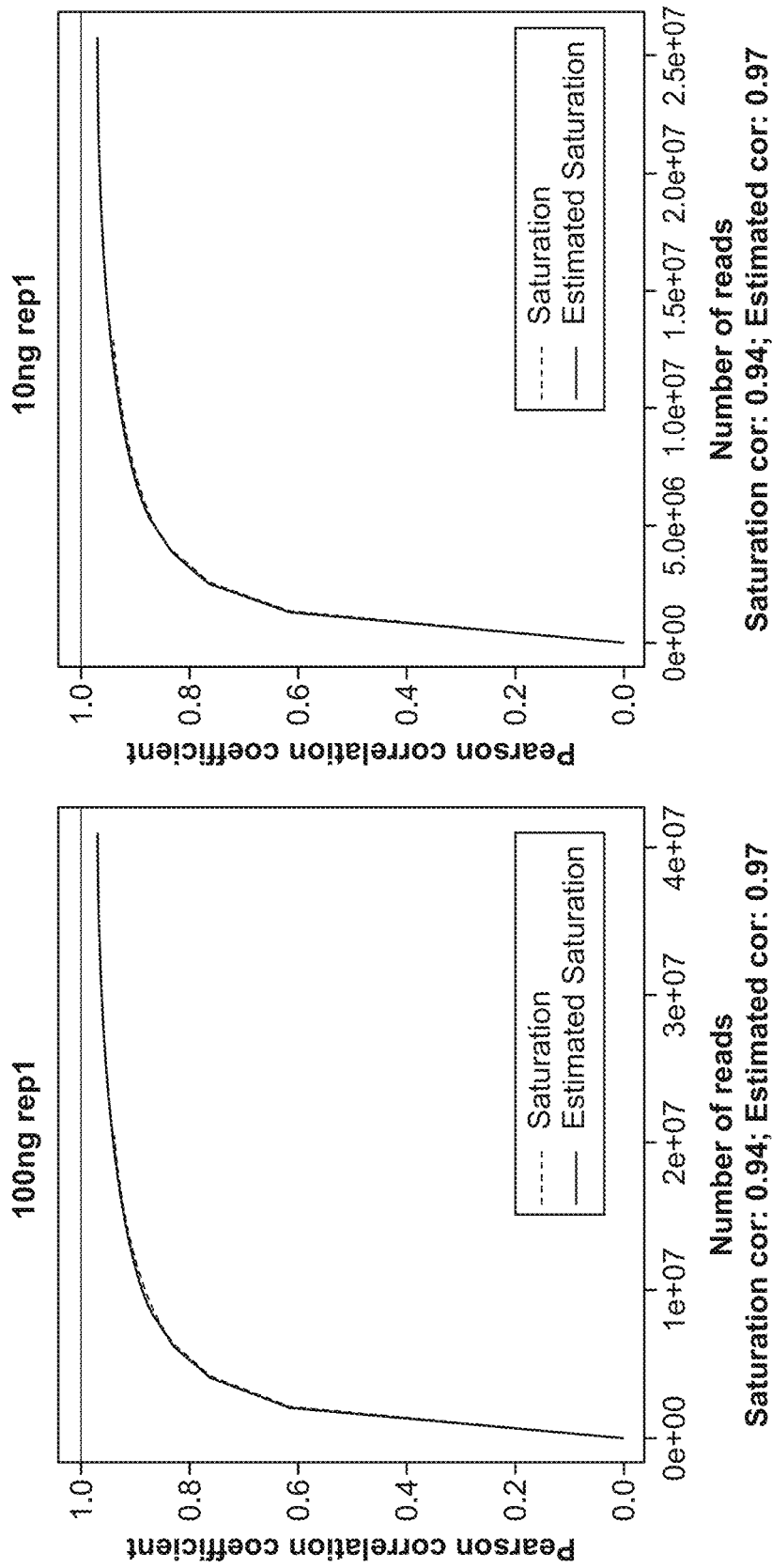
FIG. 6 shows sequencing saturation analysis and quality controls. A) The figure shows the results of the saturation analysis from the Bioconductor package MEDIPS analyzing cfMeDIP-seq data from each replicate for each input concentration from the HCT116 DNA fragmented to mimic plasma cfDNA. B) The protocol was tested in two replicates of four starting DNA concentrations (100, 10, 5, and 1 ng) of HCT116 cell line. Specificity of the reaction was calculated using methylated and unmethylated spiked-in *A. thaliana* DNA. Fold enrichment ratio was calculated using genomic regions of the fragmented HCT116 DNA (Primers for methylated testis-specific H2B, TSH2B0 and unmethylated human DNA region (GAPDH promoter)). The horizontal dotted line indicates a fold-enrichment ratio threshold of 25. Error bars represent±1 s.e.m. C) CpG Enrichment Scores of the sequenced samples show a robust enrichment of CpGs within the genomic regions from the immunoprecipitated samples compared to the input control. The CpG Enrichment Score was obtained by dividing the relative frequency of CpGs of the regions by the relative frequency of CpGs of the human genome. Error bars represent±1 s.e.m.
Figure 6C:
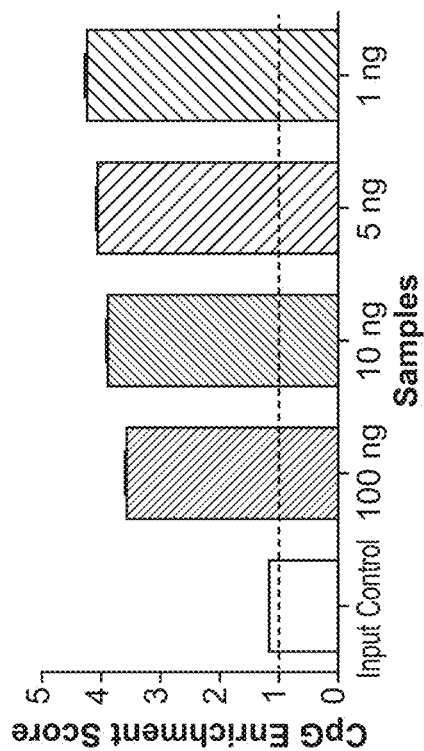
Figure 6B:
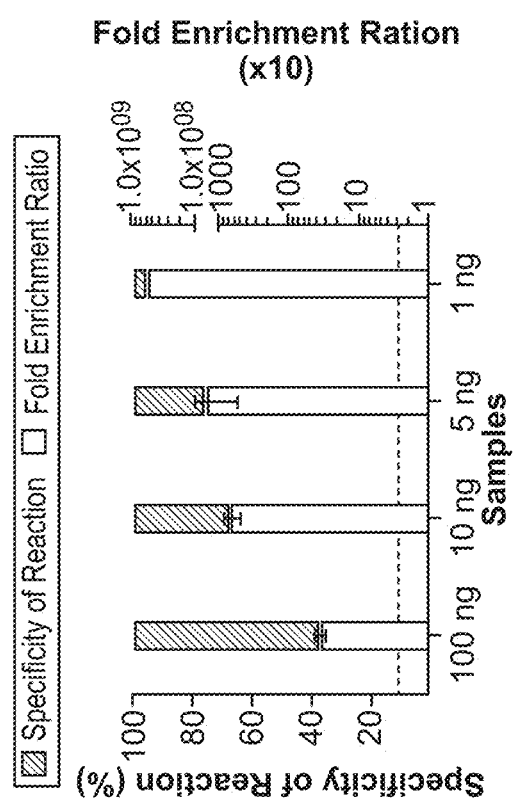

We first validated the cfMeDIP-seq protocol using DNA from human colorectal cancer cell line HCT116, sheared to a fragment size similar to that observed in cfDNA. HCT116 was chosen because of the availability of public DNA methylation data. We simultaneously performed the gold standard MeDIP-seq protocol[7] using 100 ng of sheared cell line DNA and the cfMeDIP-seq protocol using 10 ng, 5 ng, and 1 ng of the same sheared cell line DNA. This was performed in two biological replicates. For all the conditions, we obtained more than 99% specificity of the reaction (1-[recovery of spiked-in unmethylated control DNA over recovery of spiked-in methylated control DNA]), and a very high enrichment of a known methylated region over an unmethylated region (TSH2B0 and GAPDH, respectively) (FIG. 6B).

The libraries were sequenced to saturation (FIG. 6A) at around 30 to 70 million reads per library (Supplementary Table 1). The raw reads were aligned to both the human genome and the λ genome, and found virtually no alignment was found to the λ genome (Supplementary Table 1). Therefore, the addition of the exogenous λ DNA as filler DNA did not interfere with the generation of sequencing data. Finally, we calculate the CpG Enrichment Score as a quality control measure for the immunoprecipitation step[8]. All the libraries showed similar enrichment for CpGs while the input control, as expected, showed no enrichment (FIG. 6C), validating our immunoprecipitations even at extremely low inputs (1 ng).

Figure 1B:
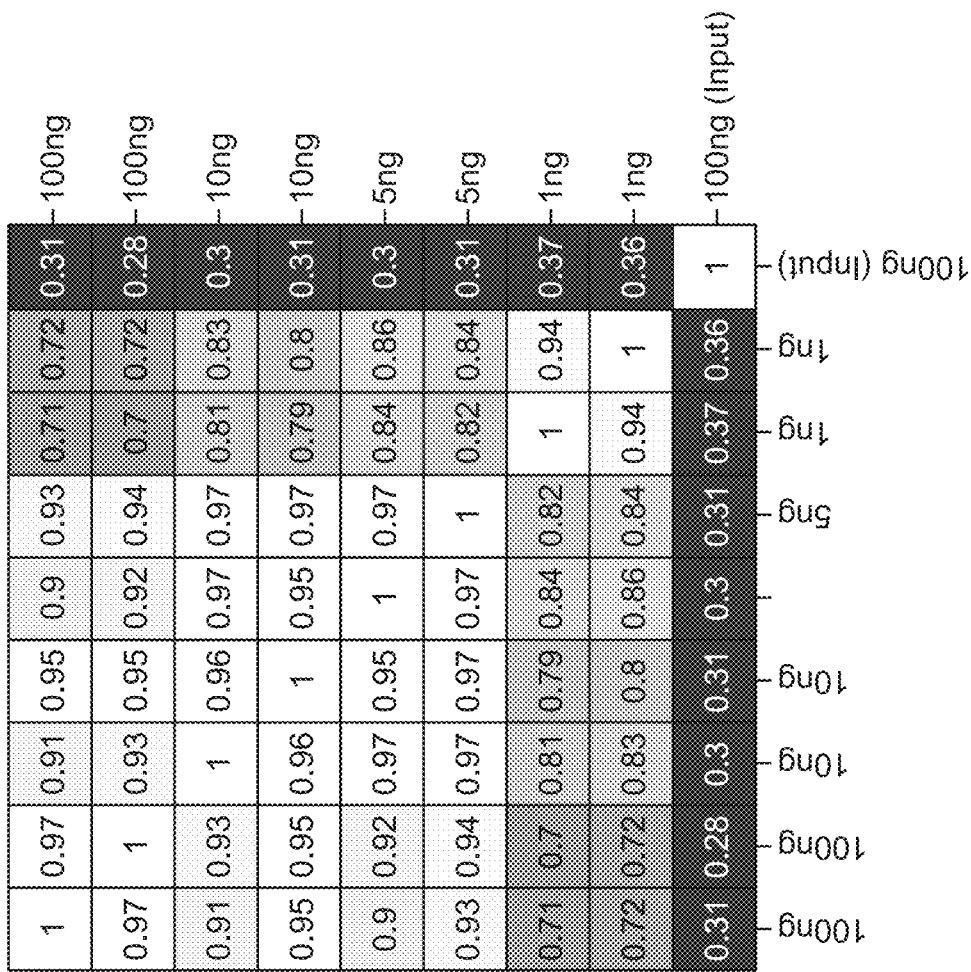
Figure 1C:
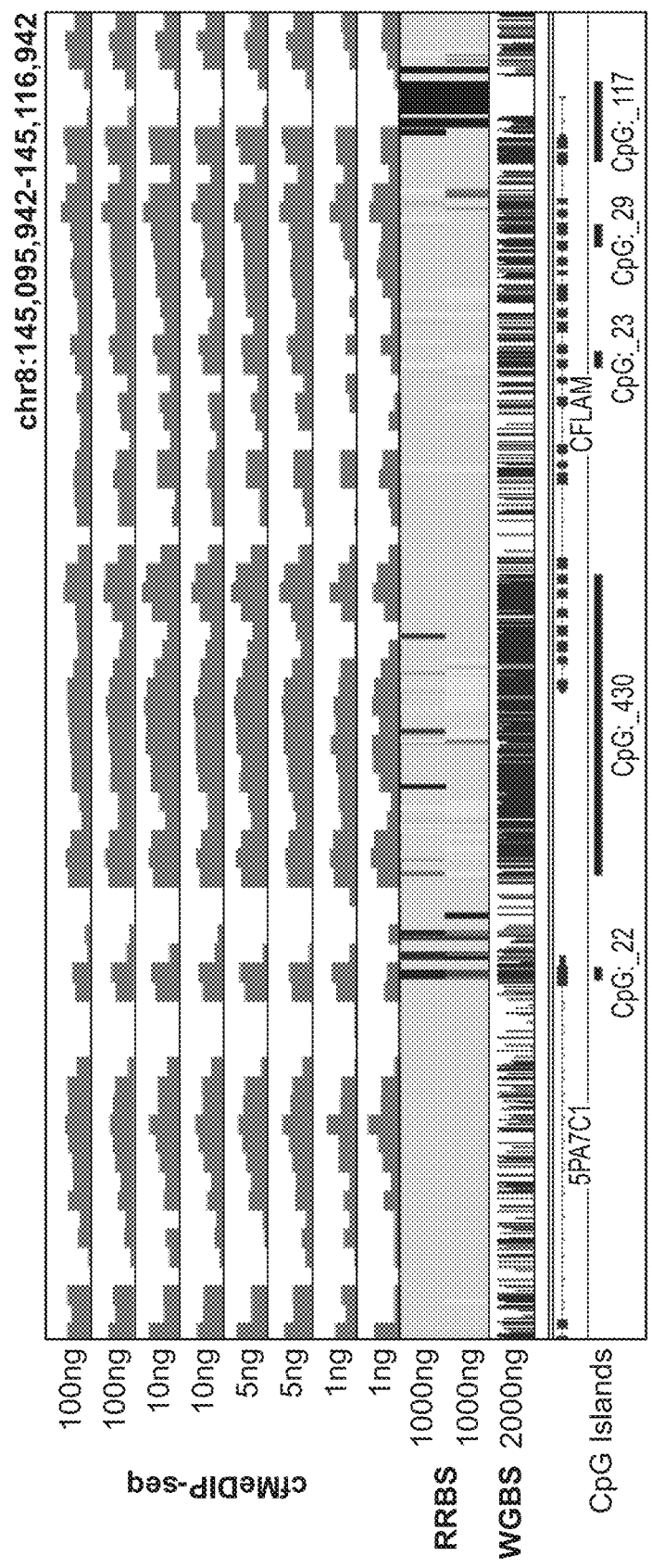

Genome-wide correlation estimates comparing different input DNA levels show that both MeDIP-seq (100 ng) and cfMeDIP-seq (10, 5, and 1 ng) methods were very robust, with Pearson correlation of at least 0.94 between any two biological replicates (FIG. 1B). The analysis also demonstrates that cfMeDIP-seq at 5 and 10 ng of input DNA can robustly recapitulate the methylation profile obtained by traditional MeDIP-seq at 100 ng (Pairwise Pearson correlation of at least 0.9) (FIG. 1B). The performance of cfMeDIP-seq at 1 ng of input DNA is reduced compared to MeDIP-seq at 100 ng but still shows a strong Pearson correlation at >0.7 (FIG. 1B). We also observed that the cfMeDIP-seq protocol recapitulates the DNA methylation profile of HCT116 using gold standard RRBS (Reduced Representation Bisulfite Sequencing) and WGBS (Whole-Genome Bisulfite Sequencing) (FIG. 1C). Altogether, our data suggests that cfMeDIP-seq is a robust protocol for genome-wide methylation mapping of fragmented and low input DNA material, such as circulating cfDNA.

cfMeDIP-seq Displays High-Sensitivity for Detection of Tumor-Derived ctDNA

Figure 1D:
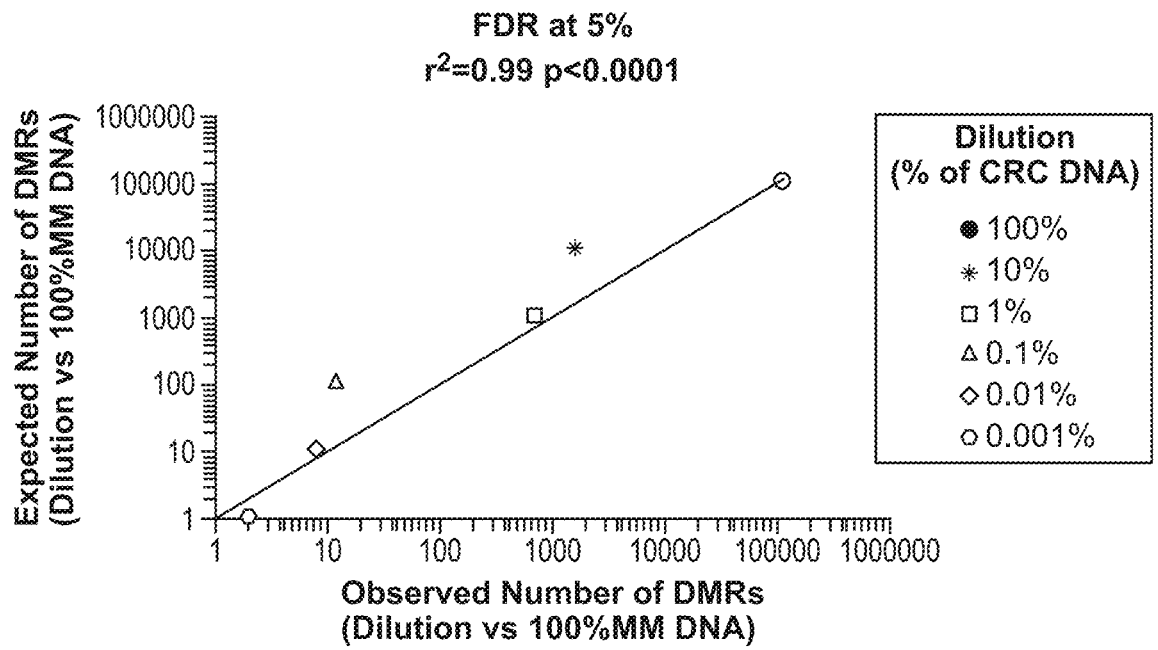
Figure 1E:
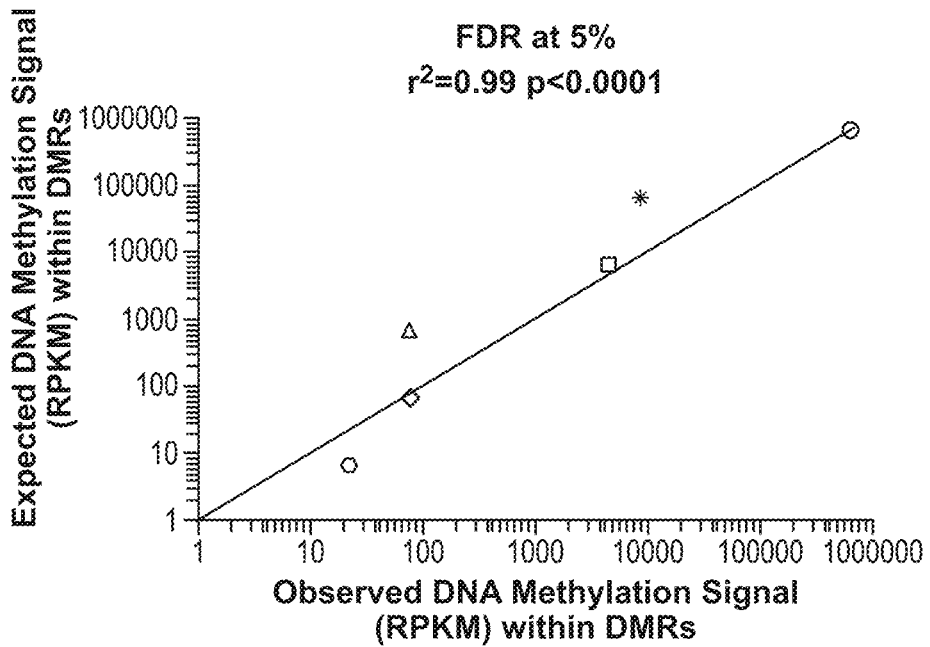
Figure 1F:
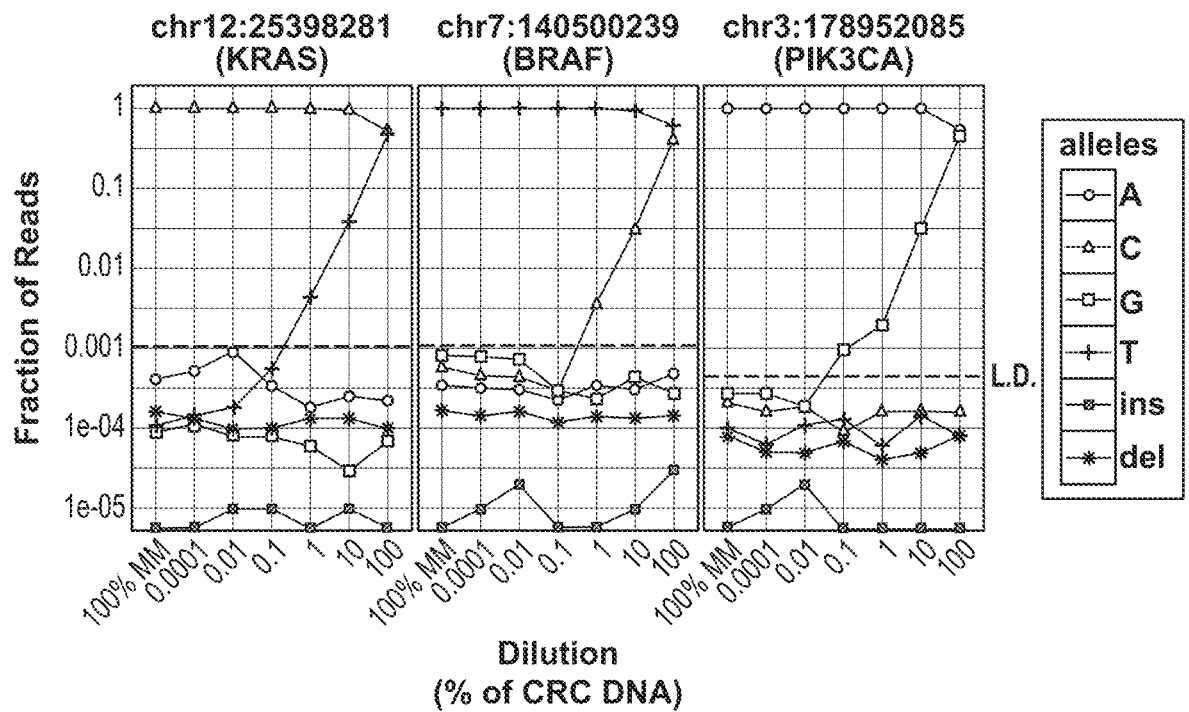

To evaluate the sensitivity of the cfMeDIP-seq protocol, we performed a serial dilution of Colorectal Cancer (CRC) HCT116 cell line DNA into a Multiple Myeloma (MM) MM1.S cell line DNA, both sheared to mimic cfDNA sizes. We diluted the CRC DNA from 100%, 10%, 1%, 0.1%, 0.01%, 0.001%, to 0% and performed cfMeDIP-seq on each of these dilutions. We also performed ultra-deep (10,000× median coverage) targeted sequencing for detection of three point mutations in the same samples. The observed number of DMRs identified at each CRC dilution point versus the pure MM DNA using a 5% False Discovery rate (FDR) threshold was almost perfectly linear ($r^2$=0.99, p<0.0001) with the expected number of DMRs based on the dilution factor (FIG. 1D) down to a 0.001% dilution. Moreover, the DNA methylation signal within these DMRs also shows almost perfect linearity ($r^2$=0.99, p<0.0001) between the observed versus expected signal (FIG. 1E; Supplementary Table 2B). In comparison, beyond the 1% dilution, ultra-deep targeted sequencing could not reliably distinguish between the CRC-specific variants and the spurious variants due to PCR or sequencing-errors (FIG. 1F; Supplementary Table 2A). Thus, cfMeDIP-seq displays excellent sensitivity for the detection of cancer-derived DNA, exceeding the performance of variant detection by ultra-deep targeted sequencing using a standard protocol.

Figure 1G:
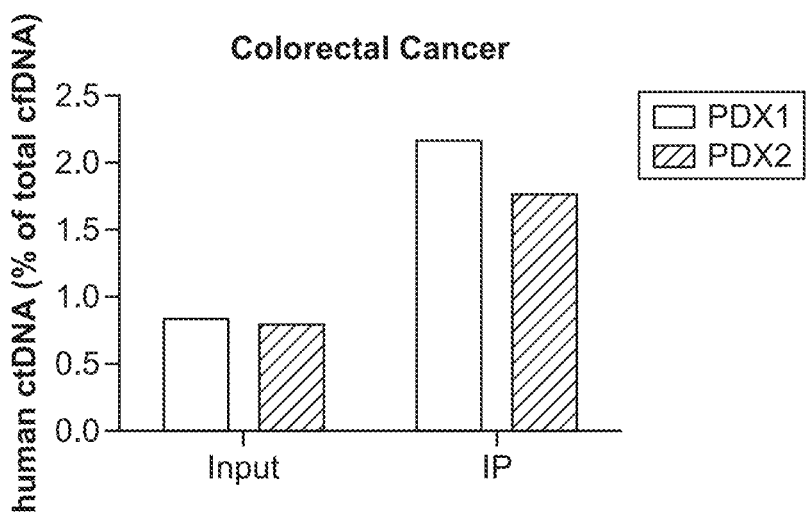

Cancer DNA is frequently hypermethylated at CpG-rich regions[17]. Since cfMeDIP-seq specifically targets methylated CpG-rich sequences, we hypothesized that ctDNA would be preferentially enriched during the immunoprecipitation procedure. To test this, we generated patient-derived xenografts (PDXs) from two colorectal cancer patients and collected the mouse plasma. Tumor-derived human cfDNA was present at less than 1% frequency within the total cfDNA pool in the input samples and at 2-fold greater abundance following immunoprecipitation (FIG. 1G; Supplementary Table 3). These results suggest that through biased sequencing of ctDNA, the cfMeDIP procedure could further increase ctDNA detection sensitivity.

Figure 2B:
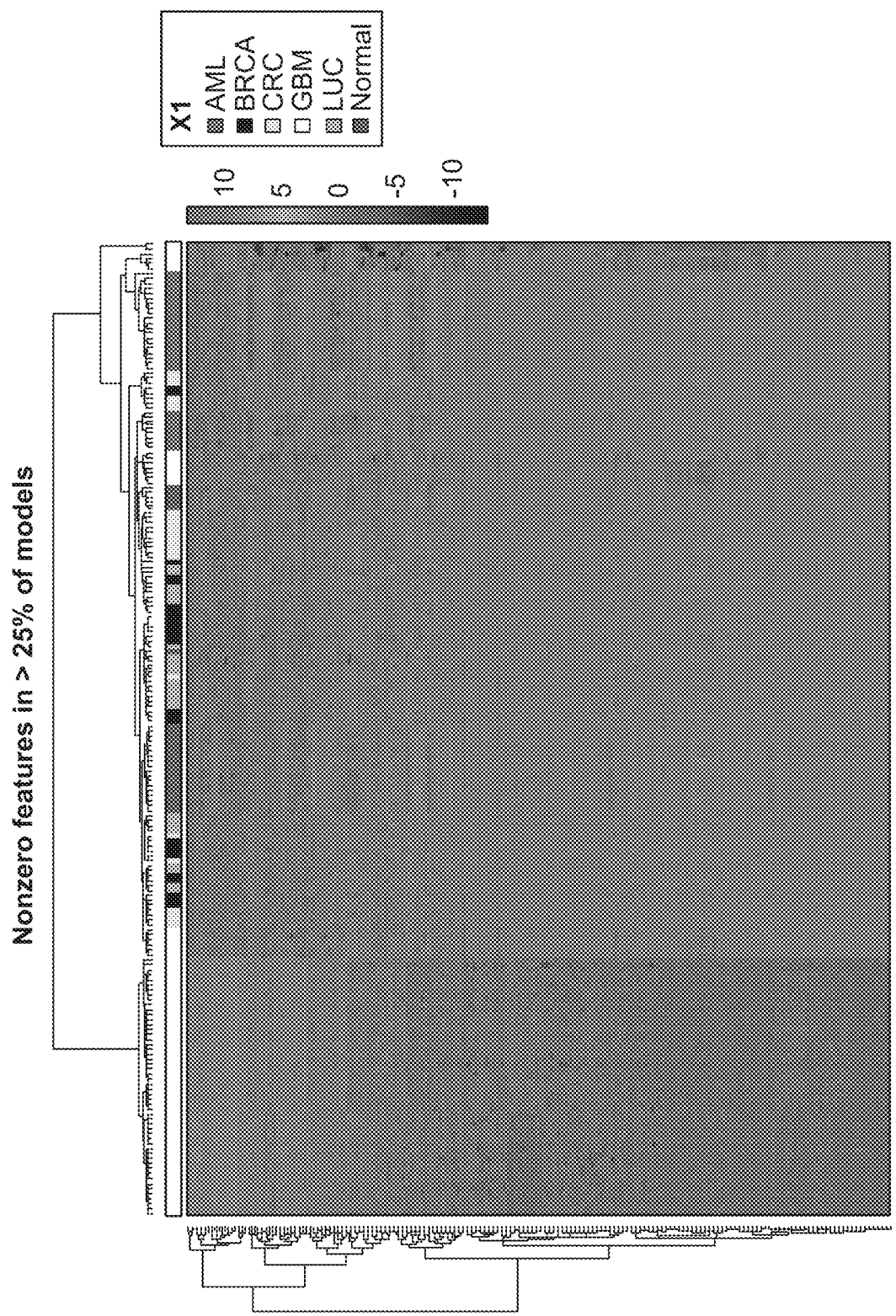
Figure 2C:
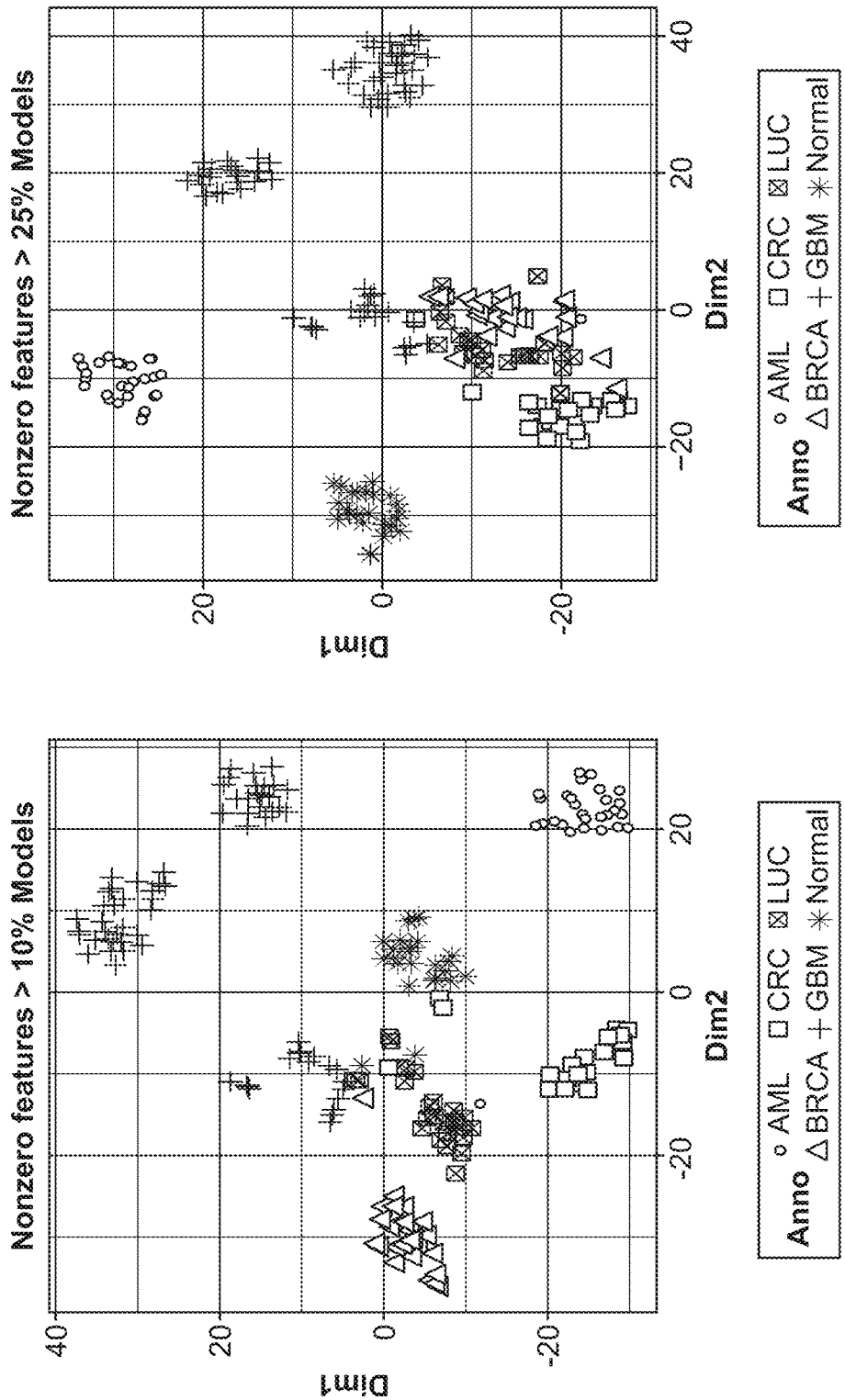
Figure 2D:
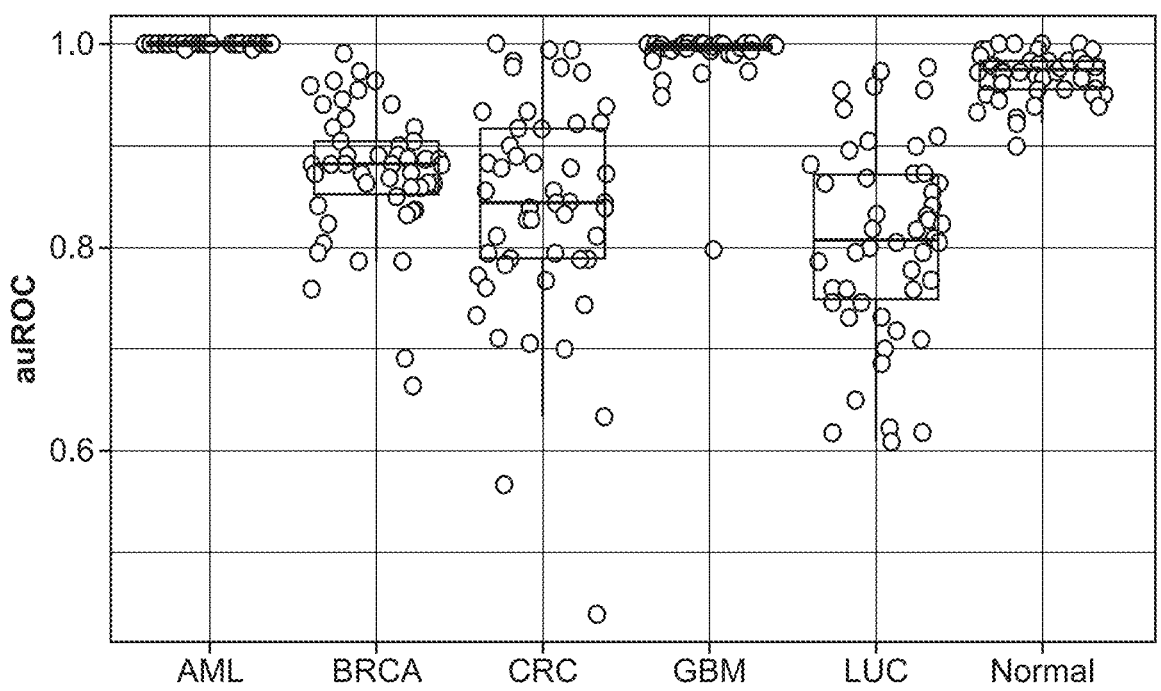

Circulating Plasma cfDNA Methylation Profile can Distinguish Between Multiple Cancer Types and Healthy Donors DNA methylation patterns are tissue-specific, and have been used to stratify cancer patients into clinically relevant disease subgroups in glioblastoma[18], ependymomas[6], colorectal[19], and breast[20, 21], among many other cancer types. We asked if cfDNA associated profiles could be used to identify tissues-of-origin for multiple tumor types. To this end, we profiled 196 samples from 5 different tumor types and normal controls from early and late stage tumors. We used linear modeling to identify the top 300 DMRs mapping to CpG shores, shelves, islands and FANTOM5 enhancers for each pairwise comparison, leading to a total of 2,100 unique DMRs (FIG. 2A). Density clustering based on t-Distributed Stochastic Neighbor Embedding (tSNE)[22] of the 196 plasma samples based on the methylation status of these features revealed distinct clustering of samples based on tissue-of-origin and tumor types (FIG. 2B,C). Using an elastic net multi-cancer classifier fit with these features (FIG. 2A), we observed highly accurate discrimination between different tumor types (FIG. 2D).

Discrimination of Disease Subtypes

We evaluated the ability of cfDNA MeDIP profiles to discriminate between disease subtypes in five distinct cases—gene expression pattern (ER status in breast cancer), copy number aberration (HER2 status in breast cancer), rearrangement (FLT3 ITD status in AML), point mutation (IDH mutation in GBM), and finally histology in lung cancer. In each case, linear models were used to select and rank features as described earlier. In each case, hierarchical clustering was used to evaluate the grouping of samples. Density clustering based on t-Distributed Stochastic Neighbor Embedding (tSNE)[22] based on the methylation status of selected features revealed distinct clustering of samples based on each of these five distinct examples of cancer subtype classification.

Detection of Cancers and Classification of Cancer Types using Machine Learning

In order to rigorously evaluate the ability of cfMeDIP profiles to detect cancers and further classify cancer types, we then conducted a set of machine learning analyses on our discovery cohort. To allow for accelerated computational analysis, we initially reduced our cfMeDIP discovery cohort to features mapping to CpG islands, shores, shelves and FANTOM5 enhancers (n=505,027 windows). We then implemented a strategy on our discovery cohort samples to derive unbiased estimates of performance, while accounting for training-set biases.

Herein, we split the discovery cohort into balanced training and test sets (80% training set, 20% test set). Using only the samples in the training set, we selected the top 300 DMRs for each class (sample type) versus other classes, based on limma-trend test statistics, and trained a series of one-versus-other-classes GLMnets using these features on the training set data. The training procedure consisted of 3 rounds of 10-Fold Cross-Validation (CV) across a grid of values for alpha and lambda with optimisation for Cohen's Kappa. The use of multiple rounds of 10-Fold CV was motivated by a desire to leverage additional randomisation for more generalisable model tuning.

Performance was then evaluated using AUROC (area under the receiver operating characteristic curve) derived from test set samples (held-out during the DMR selection and the subsequent GLMnet training/tuning steps). This process was repeated with 50 different splits of the discovery cohort into training and test sets to mitigate the influence of training-set biases. This culminated in a collection of 50 models for each one-vs other-classes comparison (480 models in total). Hereby, we refer to this collection of models as E50.

Figure 3A:
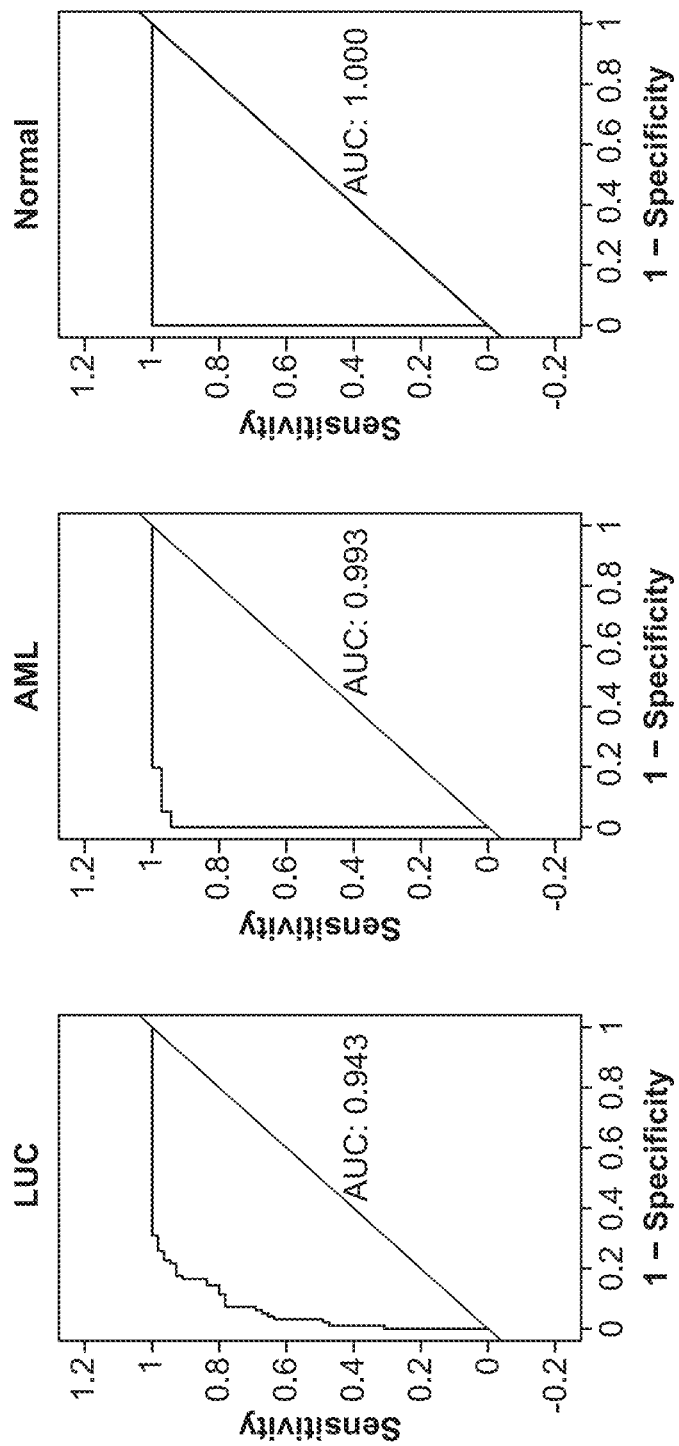
FIG. 3 shows validation of the multi-cancer classifier on independent cohorts. A) ROC curves are shown for independent validation of the multi-cancer classifier on cohorts of lung cancer (LUC) (n=55 LUC vs n=97 other), AML (n=35 AML vs n=117 other), and healthy donors (n=62 healthy donors vs n=90 other). B) ROC curves are shown for independent validation of the multi-cancer classifier on early stage LUC (n=32 stage I-II LUC vs n=97 other) and late stage LUC (n=23 stage III-IV LUC vs n=97 other).
Figure 3B:
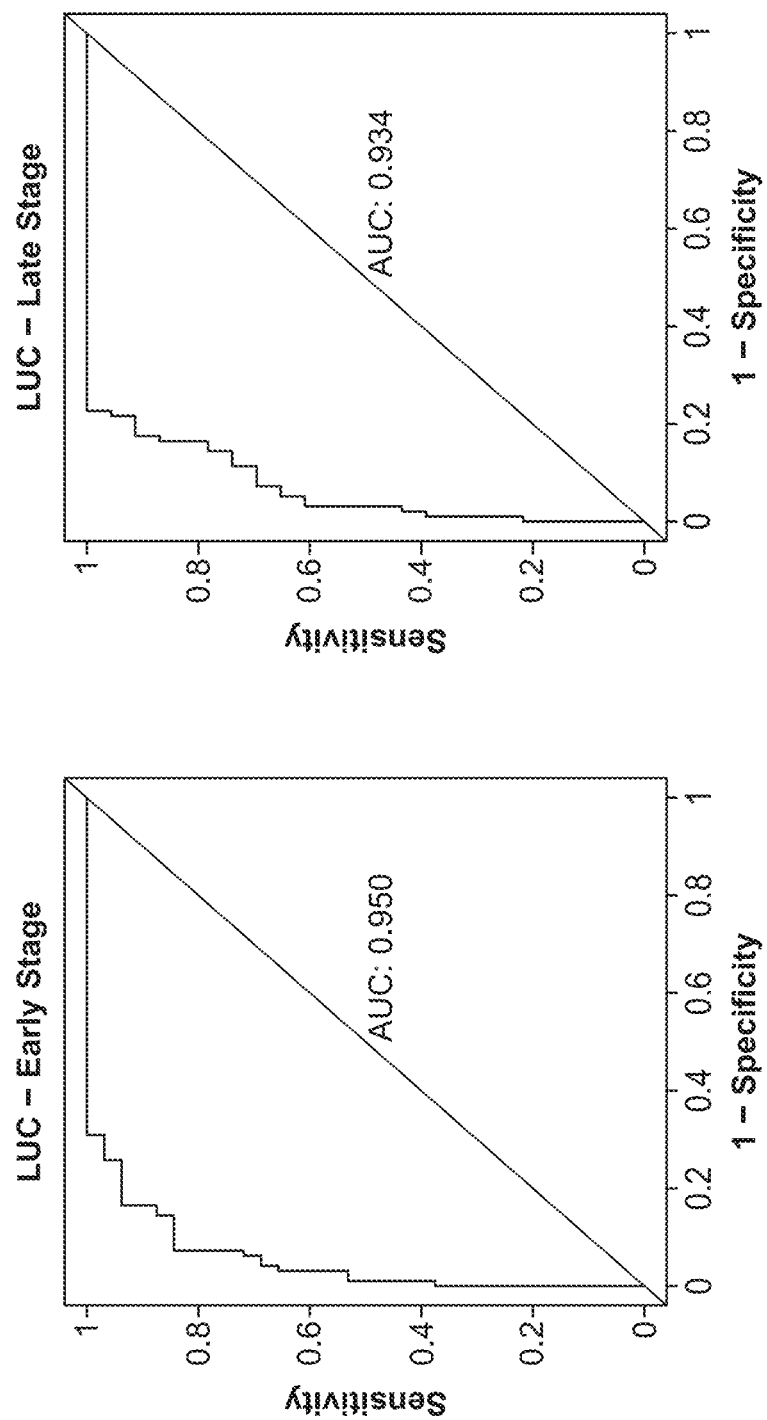
Figure 4A:
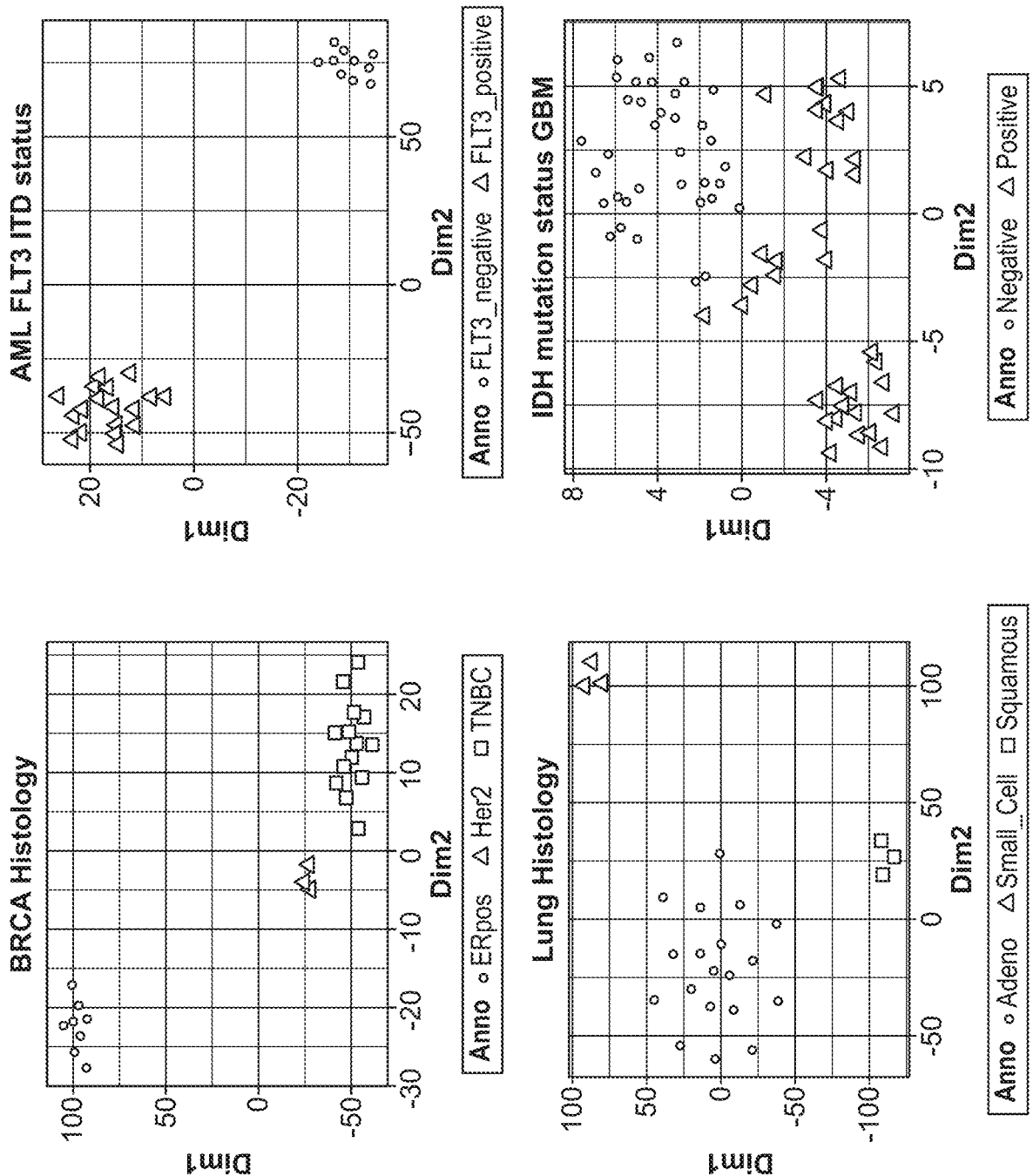
FIG. 4 shows the methylome analysis of plasma cfDNA allows tumor subtype classification. A) 2D visualizations by tSNE (t-Distributed Stochastic Neighbor Embedding) of cancer subtype associated DMRs. Breast cancer subtypes show ability to distinguish between patients harboring tumors with distinct gene expression pattern and transcription factor activity (ER status) as well as distinct tumor copy number aberrations (HER2 status). AML subtypes show ability to distinguish between patients harboring tumors with distinct rearrangements (FLT3 status). Glioblastoma multiforme (GBM) subtypes show ability to distinguish between patients harboring tumors with distinct point mutations (IDH gene mutational status). Lung cancer subtypes show ability to distinguish between patients harboring tumors with distinct histologies that have prognostic and therapeutic implications (adenocarcinoma vs. squamous carcinoma vs. small cell carcinoma). B) Heatmap showing the top DMRs that allow accurate discrimination of the three breast cancer subtypes in breast cancer plasma samples. C) Heatmap showing the top DMRs that allow accurate discrimination of the FLT3-ITD status in AML patient plasma samples. D) Heatmap showing the top DMRs that allow accurate discrimination of the IDH gene mutational status in glioblastoma multiforme (GBM) patient plasma samples. E) Heatmap showing the top DMRs that allow accurate discrimination of the three lung cancer histologies in lung cancer plasma samples.
Figure 4B:
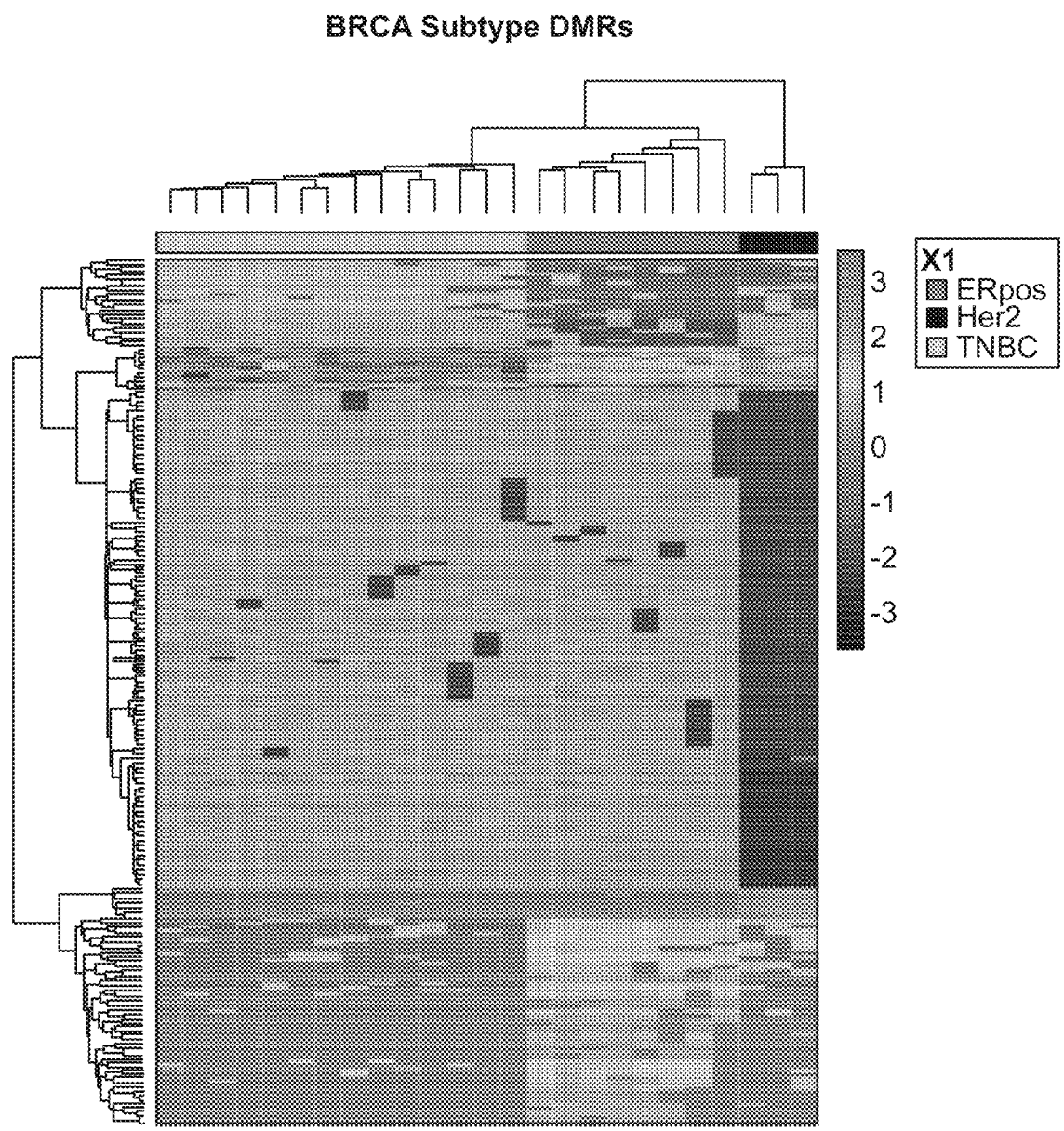
Figure 4C:
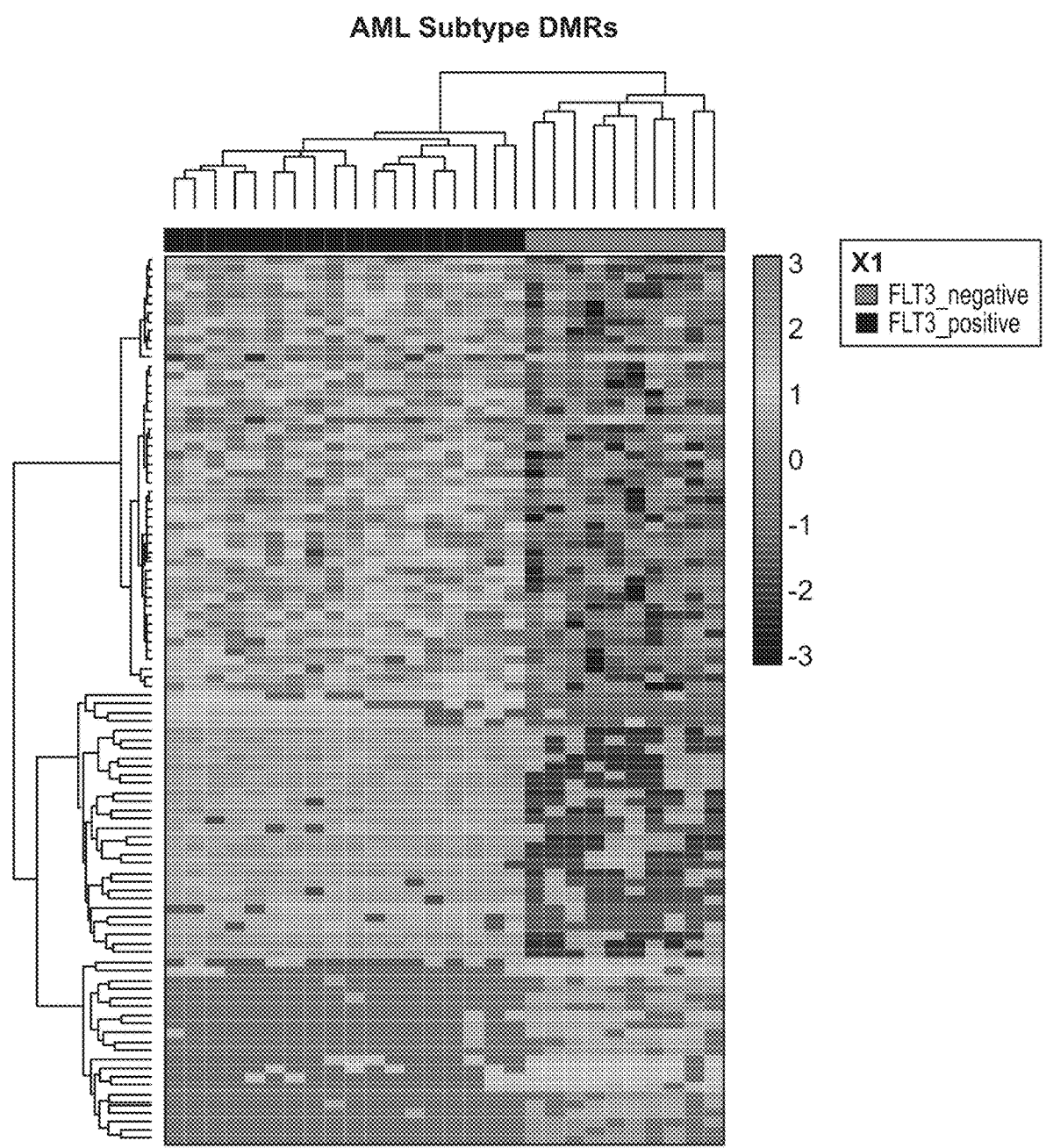
Figure 4D:
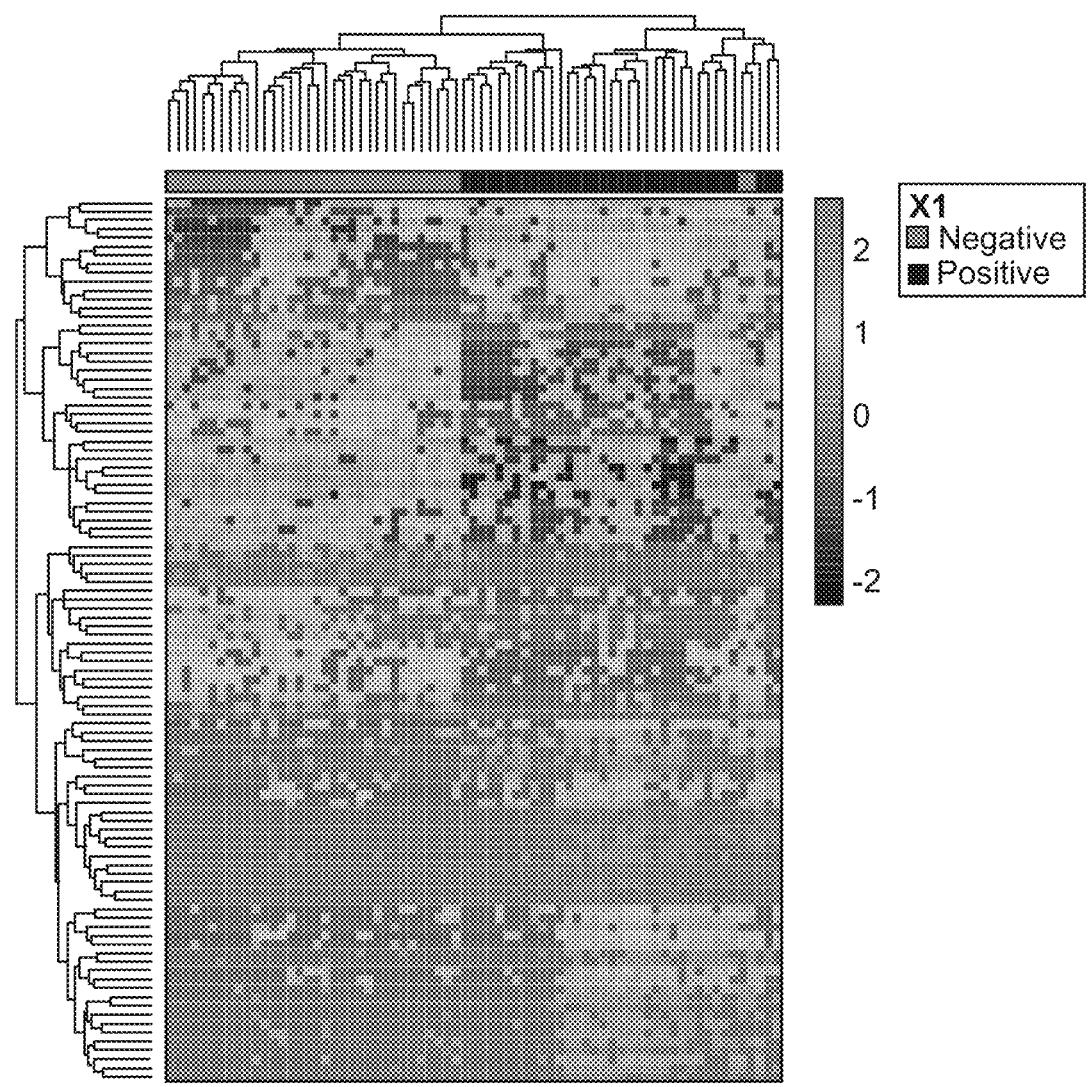
Figure 4E:
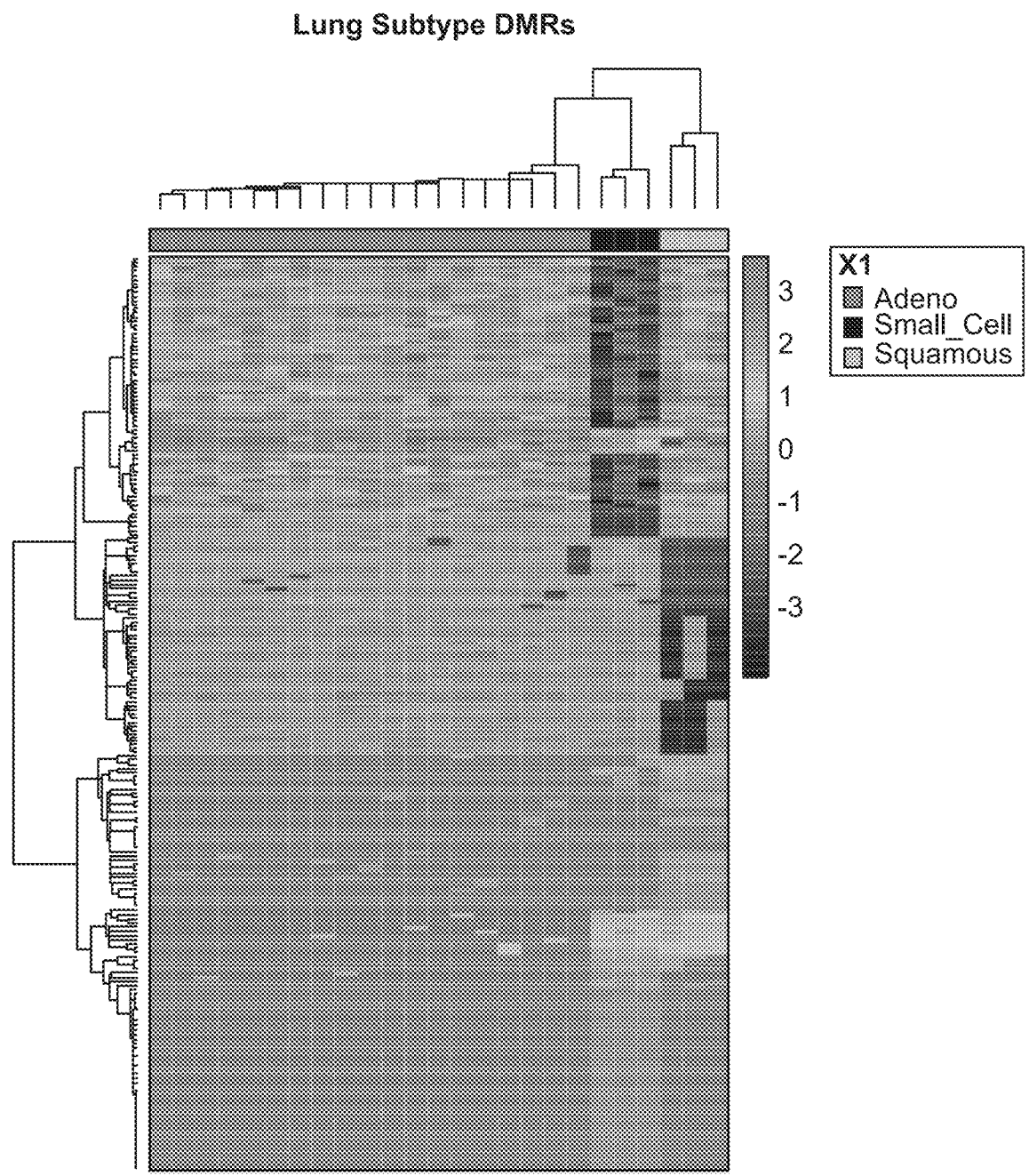

Subsequently, we evaluated performance across batches by generating a validation cohort of additional 152 plasma samples: AML (n=35), lung cancer (n=55) and healthy control (n=62) samples. For each class, we averaged the class probabilities output by the models in E50, and estimated AUROC for the one class vs. all others classes (FIG. 3A). The classifiers showed high AUROC values for the classification of AML vs others (0.993), LUC vs others (0.943) and normal vs others (1.000). This further confirmed the ability of cfMeDIP-seq coupled with a machine learning approach to accurately detect and classify tumor type. Finally, we observed that the classifiers were as accurate in early stage samples (0.950) as in late stage samples (0.934) (FIG. 3B), suggested that this approach is applicable for cancer early detection and for detection of cancer at both early stages and late stages.

Additional Advantages of cfDNA Methylome Profiling with cfMeDIP-seq

The ability of cfDNA methylation patterns to accurately represent tissue-of-origin also overcomes limitations of mutation-based assays, wherein specificity for tissues-of-origin may be low due to the recurrent nature of many potential driver mutations across cancers in different tissues [23]. Mutation based assays may also be rendered insensitive by the clonal structure of tumors, where subclonal drivers may be harder to detect by virtue of lower abundance in ctDNA[24]. Mutation based ctDNA approaches are also vulnerable to potential confounding by driver mutations in benign tissues, which have been observed[25], and documented to display evidence of positive selection[26].

Taken together, our findings—based on the largest collection of cancer cfDNA methylomes derived to date—establish cfMeDIP-seq as an efficient and cost-effective tool with the potential to influence management of cancer and early detection. The accuracy and versatility of cfMeDIP-seq may be useful to inform therapeutic decisions in settings where resistance is correlated to epigenetic alterations, such as sensitivity to androgen receptor inhibition in prostate cancer[27]. The potential opportunities for early diagnosis and screening may be particularly evident in lung cancer, a disease in which screening has already shown clinical utility but for which existing screening tests (i.e., low dose CT scanning) has significant limitations such as ionizing radiation exposure and high false positive rate.

In conclusion, our findings underscore the utility of cfDNA methylation profiles as a basis for non-invasive, cost-effective, sensitive, highly accurate early tumor detection, multi-cancer classification, and cancer subtype classification.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

TABLE 1

Number of reads and mapping efficiency of sequenced MeDIP-seq (100 ng Rep 1 and Rep 2) and cfMeDIP-seq (10 ng, 5 ng and 1 ng, Rep1 and Rep 2) libraries prepared using various starting inputs of HCT116 cell line DNA sheared to mimic cfDNA, to human (Hg19) genome and λ genome. Two biological replicates were use for starting input DNA. For starting inputs less than 100 ng, the samples were topped up with exogenous λ DNA to artificially increase the starting amount to 100 ng prior to MeDIP.

| Sample | # of raw reads | # of aligned reads to human genome (Hg19) | Mapping efficiency to human genome (Hg19) | # of aligned reads to λ genome | Mapping efficiency to λ genome |
|---|---|---|---|---|---|
| Input | 74,504,053 | 71,343,168 | 95.76 | 12 | 0.00 |
| 100 ng Replicate 1 | 55,396,238 | 50,472,273 | 91.11 | 0 | 0.00 |
| 100 ng Replicate 2 | 66,569,209 | 60,770,277 | 91.29 | 1 | 0.00 |
| 10 ng Replicate 1 | 70,054,607 | 64,020,441 | 91.39 | 0 | 0.00 |
| 10 ng Replicate 2 | 58,297,539 | 53,308,777 | 91.44 | 0 | 0.00 |
| 5 ng Replicate 1 | 65,845,430 | 60,540,743 | 91.94 | 1 | 0.00 |
| 5 ng Replicate 2 | 64,750,879 | 59,358,412 | 91.67 | 0 | 0.00 |
| 1 ng Replicate 1 | 35,102,361 | 32,258,451 | 91.90 | 0 | 0.00 |
| 1 ng Replicate 2 | 33,881,118 | 31,194,711 | 92.07 | 0 | 0.00 |

TABLE 2A

Mean coverage of ultra-deep targeted variant sequencing using dilution series of CRC cell line HCT116 DNA into MM cell line MM1.S DNA

| Dilution (% of CRC DNA) | Uncollapsed reads mean target coverage | SSCS (single strand consensus sequences) mean target coverage | DCS (duplex consensus sequences) mean target coverage |
|---|---|---|---|
| 100 | 155,964 | 4284 | 655 |
| 10 | 154,657 | 4877 | 654 |
| 1 | 154,419 | 4890 | 654 |
| 0.1 | 183,271 | 5674 | 887 |
| 0.01 | 238,291 | 8068 | 1602 |
| 0.001 | 199,766 | 7337 | 1299 |
| 0.0001 | 187,695 | 6891 | 1181 |
| 0 | 216,434 | 7721 | 1412 |

TABLE 2B

Resultant observed DMRs and DNA methylation signal from the dilution series of CRC cell line HCT116 DNA into MM cell line MM1.S DNA

| Dilution (% of CRC DNA) | Observed number of DMRs | Observed DNA methylation signal (sum of RPKMs within DMRs) |
|---|---|---|
| 100 | 111,472 | 645,683.90 |
| 10 | 1,597 | 8,775.61 |
| 1 | 692 | 4,521.60 |
| 0.1 | 12 | 75.71 |
| 0.01 | 8 | 79.73 |
| 0.001 | 2 | 22.42 |

TABLE 3

Number of reads and mapping efficiency of cfMeDIP-seq libraries of PDX and Input Control samples after aligning to human (Hg19) genome

| Sample | # of Raw reads | # of Aligned reads to human genome (Hg19) | Mapping efficiency to human genome (Hg19) |
|---|---|---|---|
| Input Control 1 | 46,857,633 | 389,073 | 0.83 |
| Input Control 2 | 35,658,454 | 283,799 | 0.80 |
| PDX 1 | 49,997,949 | 1,080,277 | 2.16 |
| PDX 2 | 34,802,767 | 614,988 | 1.77 |

REFERENCE LIST

1. Diaz, L. A., Jr. and A. Bardelli, *Liquid biopsies: genotyping circulating tumor DNA*. J Clin Oncol, 2014. 32(6): p. 579-86.
2. Lehmann-Werman, R., et al., *Identification of tissue-specific cell death using methylation patterns of circulating DNA*. Proc Natl Acad Sci USA, 2016. 113(13): p. E1826-34.
3. Visvanathan, K., et al., *Monitoring of Serum DNA Methylation as an Early Independent Marker of Response and Survival in Metastatic Breast Cancer: TBCRC 005 Prospective Biomarker Study*. J Clin Oncol, 2016: p. JCO2015662080.
4. Newman, A. M., et al., *An ultrasensitive method for quantitating circulating tumor DNA with broad patient coverage*. Nat Med, 2014. 20(5): p. 548-54.
5. Aravanis, A. M., M. Lee, and R. D. Klausner, *Next-Generation Sequencing of Circulating Tumor DNA for Early Cancer Detection*. Cell, 2017. 168(4): p. 571-574.
6. Mack, S. C., et al., *Epigenomic alterations define lethal CIMP-positive ependymomas of infancy*. Nature, 2014. 506(7489): p. 445-50.
7. Taiwo, O., et al., *Methylome analysis using MeDIP-seq with low DNA concentrations*. Nat Protoc, 2012. 7(4): p. 617-36.
8. Lienhard, M., et al., *MEDIPS: genome-wide differential coverage analysis of sequencing data derived from DNA enrichment experiments*. Bioinformatics, 2014. 30(2): p. 284-6.
9. Law, C. W., et al., *voom: Precision weights unlock linear model analysis tools for RNA-seq read counts*. Genome Biol, 2014. 15(2): p. R29.
10. Chakravarthy, A., et al., *Human Papillomavirus Drives Tumor Development Throughout the Head and Neck: Improved Prognosis Is Associated With an Immune Response Largely Restricted to the Oropharynx*. J Clin Oncol, 2016. 34(34): p. 4132-4141.
11. Hoadley, K. A., et al., *Multiplatform analysis of 12 cancer types reveals molecular classification within and across tissues of origin*. Cell, 2014. 158(4): p. 929-44.
12. Fleischhacker, M. and B. Schmidt, *Circulating nucleic acids (CNAs) and cancer—a survey*. Biochim Biophys Acta, 2007. 1775(1): p. 181-232.
13. Potter, N. T., et al., *Validation of a real-time PCR-based qualitative assay for the detection of methylated SEPT9 DNA in human plasma*. Clin Chem, 2014. 60(9): p. 1183-91.

14. Legendre, C., et al., *Whole-genome bisulfite sequencing of cell-free DNA identifies signature associated with metastatic breast cancer*. Clin Epigenetics, 2015. 7: p. 100.
15. Sun, K., et al., *Plasma DNA tissue mapping by genome-wide methylation sequencing for noninvasive prenatal, cancer, and transplantation assessments*. Proc Natl Acad Sci USA, 2015. 112(40): p. E5503-12.
16. Chan, K. C., et al., *Noninvasive detection of cancer-associated genome-wide hypomethylation and copy number aberrations by plasma DNA bisulfite sequencing*. Proc Natl Acad Sci USA, 2013. 110(47): p. 18761-8.
17. Sharma, S., T. K. Kelly, and P. A. Jones, *Epigenetics in cancer*. Carcinogenesis, 2010. 31(1): p. 27-36.
18. Sturm, D., et al., *Hotspot mutations in H3F3A and IDH1 define distinct epigenetic and biological subgroups of glioblastoma*. Cancer Cell, 2012. 22(4): p. 425-37.
19. Hinoue, T., et al., *Genome-scale analysis of aberrant DNA methylation in colorectal cancer*. Genome Res, 2012. 22(2): p. 271-82.
20. Stirzaker, C., et al., *Methylome sequencing in triple-negative breast cancer reveals distinct methylation clusters with prognostic value*. Nat Commun, 2015. 6: p. 5899.
21. Fang, F., et al., *Breast cancer methylomes establish an epigenomic foundation for metastasis*. Sci Transl Med, 2011. 3(75): p. 75ra25.
22. Laurens van der Maaten, G. H., *Visualizing Data using t-SNE*. Journal of Machine Learning Research, 2008. 9: p. 2579-2605.
23. Kandoth, C., et al., *Mutational landscape and significance across 12 major cancer types*. Nature, 2013. 502 (7471): p. 333-9.
24. McGranahan, N., et al., *Clonal status of actionable driver events and the timing of mutational processes in cancer evolution*. Sci Transl Med, 2015. 7(283): p. 283ra54.
25. Zauber, P., S. Marotta, and M. Sabbath-Solitare, *KRAS gene mutations are more common in colorectal villous adenomas and in situ carcinomas than in carcinomas*. Int J Mol Epidemiol Genet, 2013. 4(1): p. 1-10.
26. Martincorena, I., et al., *Tumor evolution. High burden and pervasive positive selection of somatic mutations in normal human skin*. Science, 2015. 348(6237): p. 880-6.
27. Beltran, H., et al., *Divergent clonal evolution of castration-resistant neuroendocrine prostate cancer.* 2016. 22(3): p. 298-305.

The invention claimed is:
1. A method comprising:
  (a) providing a sample of cell-free DNA from a subject;
  (b) adding a first amount of filler DNA to the sample, wherein at least a portion of the filler DNA is methylated, and wherein the first amount of filler DNA is from about 20 nanograms (ng) to about 100 ng;
  (c) capturing cell-free methylated DNA using a binder selective for methylated polynucleotides;
  (d) sequencing the captured cell-free methylated DNA to generate a plurality of sequencing reads; and
  (e) computer processing the plurality of sequencing reads to obtain a methylation profile of the subject.
2. The method of claim 1, wherein the sample is from the subject's blood or plasma.
3. The method of claim 1, further comprising: (f) processing the methylation profile of the subject to a reference methylation profile using a machine-learning derived classifier.
4. The method of claim 3, wherein the classifier is an elastic net classifier, lasso, support vector machine, random forest, or neural network.
5. The method of claim 3, wherein the reference methylation profile is derived from a database of Differentially Methylated Regions (DMRs) between healthy and cancerous individuals.
6. The method of claim 3, wherein the reference methylation profile is limited to those regions which are differentially methylated as between healthy and cancerous individuals in DNA derived from cell-free DNA.
7. The method of claim 3, wherein the reference methylation profile is limited to those regions which are differentially methylated as between healthy and cancerous individuals in DNA derived from blood plasma.
8. The method of claim 1, wherein the sample has less than 100 ng, 75 ng, or 50 ng of cell-free DNA.
9. The method of claim 1, wherein the first amount of filler DNA comprises between about 5% and about 50% methylated filler DNA.
10. The method of claim 1, wherein the first amount of filler DNA is from about 30 ng to about 100 ng.
11. The method of claim 1, wherein step (c) comprises immunoprecipitating the cell-free methylated DNA using an antibody.
12. The method of claim 1, further comprising, prior to step (c), adding a second amount of control DNA to the sample for confirming the capturing of the cell-free methylated DNA.
13. The method of claim 1, further comprising identifying a presence of DNA from cancer cells, and identifying cancer cell tissue of origin.
14. The method of claim 13, wherein identifying the cancer cell tissue of origin further includes identifying a cancer subtype.
15. The method of claim 14, wherein the cancer subtype differentiates the cancer based on stage, histology, gene expression pattern, copy number aberration, rearrangement, or point mutational status.
16. The method of claim 1, wherein the computer processing in step (e) is carried out genome-wide.
17. The method of claim 1, wherein the computer processing in step (e) is restricted to specific regulatory regions.
18. The method of claim 17, wherein the regulatory regions are FANTOM5 enhancers, CpG Islands, CpG shores, CpG Shelves, or any combination of the foregoing.
19. The method of claim 1, wherein the first amount of filler DNA comprises at least 10% methylated filler DNA.
20. The method of claim 1, wherein the first amount of filler DNA comprises between about 15% to about 30% methylated filler DNA.
21. The method of claim 1, wherein the first amount of filler DNA is from about 50 ng to about 100 ng.
22. A method for identifying a cancer subtype in a subject, the method comprising:
  (a) adding a first amount of filler DNA to a sample of cell-free DNA obtained from the subject, wherein at least a portion of the filler DNA is methylated, and wherein the first amount of filler DNA is from about 20 nanograms (ng) to about 100 ng;
  (b) capturing cell-free methylated DNA using a binder selective for methylated polynucleotides and sequencing the captured cell-free methylated DNA to generate a plurality of sequencing reads;
  (c) computer processing the plurality of sequencing reads to obtain a methylated profile of the subject; and

(d) computer processing the methylation profile with a reference methylation profile to identify a cancer subtype and cancer cell tissue of origin in the subject.

\* \* \* \* \*